(12) United States Patent
Hayakawa et al.

(10) Patent No.: US 6,221,636 B1
(45) Date of Patent: Apr. 24, 2001

(54) METHOD FOR PRODUCING L-LYSINE

(75) Inventors: Atsushi Hayakawa; Masakazu Sugimoto; Yasuhiko Yoshihara; Tsuyoshi Nakamatsu, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 08/985,916

(22) Filed: Dec. 5, 1997

(30) Foreign Application Priority Data

Dec. 5, 1996 (JP) .................................................... 8-325658

(51) Int. Cl.⁷ .............................. C12P 13/08; C12N 1/20; C12N 15/00; C07H 21/04
(52) U.S. Cl. ................ 435/115; 435/252.32; 435/320.1; 536/23.2
(58) Field of Search .............................. 435/115, 252.32, 435/320.1; 536/23.2

(56) References Cited

U.S. PATENT DOCUMENTS

| 4,861,722 | * | 8/1989 | Sano et al. ....................... 435/252.32 |
| 4,980,285 | * | 12/1990 | Sano et al. ........................... 435/108 |
| 5,688,671 | * | 11/1997 | Sugimoto et al. .................... 435/115 |
| 5,804,414 | * | 9/1998 | Moriya et al. ....................... 435/69.1 |

FOREIGN PATENT DOCUMENTS

| 406261766A | * | 9/1994 | (JP) . |
| 94/25605 | * | 11/1994 | (WO) . |
| 96/40934 | * | 12/1996 | (WO) . |

OTHER PUBLICATIONS

Rudinger (Jun. 1976) Characteristics of the amino acids as components of a peptide hormone sequence. In: Peptide Hormones. Ed. J. A. Parsons. University Park Press, Baltimore, MD. pp. 1–7.*

Ngo et al. (Jan. 1994) Computational complexity, protein structure prediction, and the ILevinthal paradox. In: The Protein Folding Problem and Tertiary Structure Prediction. Eds. Merz et al. Birkhauser et al., Boston, MA. pp. 491–495.*

Thorton et al. (Sep. 1995) Protein Engineering: Editorial Overview. Current Opinion in Biotechnology 6(4): 367–369.*

Wallace (Apr. 1993) Understanding cytochrome c function: engineering protein structure by semisynthesis. The FASEB Journal 7: 505–515.*

Cremer et al. (Jan. 1988) Regulation of enzymes of lysine biosynthesis in Corynebacterium glutamicum. J. Gen. Microbiol. 134 (12): 3221–3229.*

* cited by examiner

*Primary Examiner*—Einar Stole
(74) *Attorney, Agent, or Firm*—Oblon, Spivak, McClelland, Maier & Neustadt, P.C.

(57) ABSTRACT

A recombinant DNA autonomously replicable in cells of coryneform bacteria, comprising a DNA sequence coding for an aspartokinase in which feedback inhibition by L-lysine and L-threonine is substantially desensitized, and a DNA sequence coding for a diaminopimelate decarboxylase; a coryneform bacterium harboring an aspartokinase in which feedback inhibition by L-lysine and L-threonine is substantially desensitized, and comprising an enhanced DNA sequence coding for a diaminopimelate decarboxylase; and a method for producing L-lysine comprising the steps of cultivating the coryneform bacterium in an appropriate medium to allow L-lysine to be produced and accumulated in a culture of the bacterium, and collecting L-lysine from the culture.

22 Claims, 13 Drawing Sheets

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 23 bases
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "synthetic DNA"

(iv) ANTI-SENSE: no (xi) SEQUENCE DESCRIPTION: SEQ ID NO: 1:

TCGCGAAGTA GCACCTGTCA CTT                                             23

(2) INFORMATION FOR SEQ ID NO:2:

(i) SEQUENCE CHARACTERISTICS:
       (A) LENGTH: 21 bases
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "synthetic DNA"

(iv) ANTI-SENSE: yes (xi) SEQUENCE DESCRIPTION: SEQ ID NO: 2:

ACGGAATTCA ATCTTACGGC C                                               21

(2) INFORMATION FOR SEQ ID NO:3:

(i) SEQUENCE CHARACTERISTICS:
       (A) LENGTH: 1643 bases
       (B) TYPE: nucleic acid
       (C) STRANDEDNESS: double
       (D) TOPOLOGY: linear (ii) MOLECULE TYPE: genomic DNA (vi) ORIGINAL SOURCE:
       (A) ORGANISM: Brevibacterium lactofermentum
       (B) STRAIN: ATCC 13869

(xi) SEQUENCE DESCRIPTION: SEQ ID NO: 3:

TCGCGAAGTA GCACCTGTCA CTTTTGTCTC AAATATTAAA TCGAATATCA ATATACGGTC     60

TGTTTATTGG AACGCATCCC AGTGGCTGAG ACGCATCCGC TAAAGCCCCA GGAACCCTGT    120

GCAGAAAGAA AACACTCCTC TGGCTAGGTA GACACAGTTT ATAAAGGTAG AGTTGAGCGG    180

GTAACTGTCA GCACGTAGAT CGAAAGGTGC ACAAAGGTGG CCCTGGTCGT ACAGAAATAT    240

GGCGGTTCCT CGCTTGAGAG TGCGGAACGC ATTAGAAACG TCGCTGAACG GATCGTTGCC    300

ACCAAGAAGG CTGGAAATGA TGTCGTGGTT GTCTGCTCCG CAATGGGAGA CACCACGGAT    360

GAACTTCTAG AACTTGCAGC GGCAGTGAAT CCCGTTCCGC CAGCTCGTGA AATGGATATG    420

CTCCTGACTG CTGGTGAGCG TATTTCTAAC GCTCTCGTCG CCATGGCTAT TGAGTCCCTT    480

GGCGCAGAAG CTCAATCTTT CACTGGCTCT CAGGCTGGTG TGCTCACCAC CGAGCGCCAC    540

GGAAACGCAC GCATTGTTGA CGTCACACCG GGTCGTGTGC GTGAAGCACT CGATGAGGGC    600

```
AAGATCTGCA TTGTTGCTGG TTTTCAGGGT GTTAATAAAG AAACCCGCGA TGTCACCACG    660

TTGGGTCGTG GTGGTTCTGA CACCACTGCA GTTGCGTTGG CAGCTGCTTT GAACGCTGAT    720

GTGTGTGAGA TTTACTCGGA CGTTGACGGT GTGTATACCG CTGACCCGCG CATCGTTCCT    780

AATGCACAGA AGCTGAAAAA GCTCAGCTTC AAGAAATGC TGGAACTTGC TGCTGTTGGC     840

TCCAAGATTT TGGTGCTGCG CAGTGTTGAA TACGCTCGTG CATTCAATGT GCCACTTCGC    900

GTACGCTCGT CTTATAGTAA TGATCCCGGC ACTTTGATTG CCGGCTCTAT GGAGGATATT    960

CCTGTGGAAG AAGCAGTCCT TACCGGTGTC GCAACCGACA AGTCCGAAGC CAAAGTAACC   1020

GTTCTGGGTA TTTCCGATAA GCCAGGCGAG GCTGCCAAGG TTTTCCGTGC GTTGGCTGAT   1080

GCAGAAATCA ACATTGACAT GGTTCTGCAG AACGTCTCCT CTGTGGAAGA CGGCACCACC   1140

GACATCACGT TCACCTGCCC TCGCGCTGAC GGACGCCGTG CGATGGAGAT CTTGAAGAAG   1200

CTTCAGGTTC AGGGCAACTG GACCAATGTG CTTTACGACG ACCAGGTCGG CAAAGTCTCC   1260

CTCGTGGGTG CTGGCATGAA GTCTCACCCA GGTGTTACCG CAGAGTTCAT GGAAGCTCTG   1320

CGCGATGTCA ACGTGAACAT CGAATTGATT TCCACCTCTG AGATCCGCAT TTCCGTGCTG   1380

ATCCGTGAAG ATGATCTGGA TGCTGCTGCA CGTGCATTGC ATGAGCAGTT CCAGCTGGGC   1440

GGCGAAGACG AAGCCGTCGT TTATGCAGGC ACCGGACGCT AAAGTTTTAA AGGAGTAGTT   1500

TTACAATGAC CACCATCGCA GTTGTTGGTG CAACCGGCCA GGTCGGCCAG GTTATGCGCA   1560

CCCTTTTGGA AGAGCGCAAT TTCCCAGCTG ACACTGTTCG TTTCTTTGCT TCCCCGCGTT   1620

CCGCAGGCCG TAAGATTGAA TTC                                          1643

(2) INFORMATION FOR SEQ ID NO:4:

(i) SEQUENCE CHARACTERISTICS:
        (A) LENGTH: 1643 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
         (A) ORGANISM: Brevibacterium lactofermentum
         (B) STRAIN: ATCC 13869

(ix) FEATURE:
         (A) NAME/KEY: CDS
         (B) LOCATION: 217..1482

(xi) SEQUENCE DESCRIPTION: SEQ ID NO: 4:

TCGCGAAGTA GCACCTGTCA CTTTTGTCTC AAATATTAAA TCGAATATCA ATATACGGTC     60

TGTTTATTGG AACGCATCCC AGTGGCTGAG ACGCATCCGC TAAAGCCCCA GGAACCCTGT    120

GCAGAAAGAA AACACTCCTC TGGCTAGGTA GACACAGTTT ATAAAGGTAG AGTTGAGCGG    180

GTAACTGTCA GCACGTAGAT CGAAAGGTGC ACAAAG GTG GCC CTG GTC GTA CAG      234
                                        Met Ala Leu Val Val Gln
                                         1                  5

AAA TAT GGC GGT TCC TCG CTT GAG AGT GCG GAA CGC ATT AGA AAC GTC      282
Lys Tyr Gly Gly Ser Ser Leu Glu Ser Ala Glu Arg Ile Arg Asn Val
             10                  15                  20

GCT GAA CGG ATC GTT GCC ACC AAG AAG GCT GGA AAT GAT GTC GTG GTT      330
Ala Glu Arg Ile Val Ala Thr Lys Lys Ala Gly Asn Asp Val Val Val
         25                  30                  35

GTC TGC TCC GCA ATG GGA GAC ACC ACG GAT GAA CTT CTA GAA CTT GCA      378
Val Cys Ser Ala Met Gly Asp Thr Thr Asp Glu Leu Leu Glu Leu Ala
     40                  45                  50
```

```
GCG GCA GTG AAT CCC GTT CCG CCA GCT CGT GAA ATG GAT ATG CTC CTG      426
Ala Ala Val Asn Pro Val Pro Pro Ala Arg Glu Met Asp Met Leu Leu
 55              60              65              70

ACT GCT GGT GAG CGT ATT TCT AAC GCT CTC GTC GCC ATG GCT ATT GAG      474
Thr Ala Gly Glu Arg Ile Ser Asn Ala Leu Val Ala Met Ala Ile Glu
             75              80              85

TCC CTT GGC GCA GAA GCT CAA TCT TTC ACT GGC TCT CAG GCT GGT GTG      522
Ser Leu Gly Ala Glu Ala Gln Ser Phe Thr Gly Ser Gln Ala Gly Val
         90              95             100

CTC ACC ACC GAG CGC CAC GGA AAC GCA CGC ATT GTT GAC GTC ACA CCG      570
Leu Thr Thr Glu Arg His Gly Asn Ala Arg Ile Val Asp Val Thr Pro
        105             110             115

GGT CGT GTG CGT GAA GCA CTC GAT GAG GGC AAG ATC TGC ATT GTT GCT      618
Gly Arg Val Arg Glu Ala Leu Asp Glu Gly Lys Ile Cys Ile Val Ala
    120             125             130

GGT TTT CAG GGT GTT AAT AAA GAA ACC CGC GAT GTC ACC ACG TTG GGT      666
Gly Phe Gln Gly Val Asn Lys Glu Thr Arg Asp Val Thr Thr Leu Gly
135             140             145             150

CGT GGT GGT TCT GAC ACC ACT GCA GTT GCG TTG GCA GCT GCT TTG AAC      714
Arg Gly Gly Ser Asp Thr Thr Ala Val Ala Leu Ala Ala Ala Leu Asn
                155             160             165

GCT GAT GTG TGT GAG ATT TAC TCG GAC GTT GAC GGT GTG TAT ACC GCT      762
Ala Asp Val Cys Glu Ile Tyr Ser Asp Val Asp Gly Val Tyr Thr Ala
            170             175             180

GAC CCG CGC ATC GTT CCT AAT GCA CAG AAG CTG GAA AAG CTC AGC TTC      810
Asp Pro Arg Ile Val Pro Asn Ala Gln Lys Leu Glu Lys Leu Ser Phe
        185             190             195

GAA GAA ATG CTG GAA CTT GCT GCT GTT GGC TCC AAG ATT TTG GTG CTG      858
Glu Glu Met Leu Glu Leu Ala Ala Val Gly Ser Lys Ile Leu Val Leu
    200             205             210

CGC AGT GTT GAA TAC GCT CGT GCA TTC AAT GTG CCA CTT CGC GTA CGC      906
Arg Ser Val Glu Tyr Ala Arg Ala Phe Asn Val Pro Leu Arg Val Arg
215             220             225             230

TCG TCT TAT AGT AAT GAT CCC GGC ACT TTG ATT GCC GGC TCT ATG GAG      954
Ser Ser Tyr Ser Asn Asp Pro Gly Thr Leu Ile Ala Gly Ser Met Glu
                235             240             245

GAT ATT CCT GTG GAA GAA GCA GTC CTT ACC GGT GTC GCA ACC GAC AAG     1002
Asp Ile Pro Val Glu Glu Ala Val Leu Thr Gly Val Ala Thr Asp Lys
            250             255             260

TCC GAA GCC AAA GTA ACC GTT CTG GGT ATT TCC GAT AAG CCA GGC GAG     1050
Ser Glu Ala Lys Val Thr Val Leu Gly Ile Ser Asp Lys Pro Gly Glu
        265             270             275

GCT GCC AAG GTT TTC CGT GCG TTG GCT GAT GCA GAA ATC AAC ATT GAC     1098
Ala Ala Lys Val Phe Arg Ala Leu Ala Asp Ala Glu Ile Asn Ile Asp
    280             285             290

ATG GTT CTG CAG AAC GTC TCC TCT GTG GAA GAC GGC ACC ACC GAC ATC     1146
Met Val Leu Gln Asn Val Ser Ser Val Glu Asp Gly Thr Thr Asp Ile
295             300             305             310

ACG TTC ACC TGC CCT CGC GCT GAC GGA CGC CGT GCG ATG GAG ATC TTG     1194
Thr Phe Thr Cys Pro Arg Ala Asp Gly Arg Arg Ala Met Glu Ile Leu
                315             320             325

AAG AAG CTT CAG GTT CAG GGC AAC TGG ACC AAT GTG CTT TAC GAC GAC     1242
Lys Lys Leu Gln Val Gln Gly Asn Trp Thr Asn Val Leu Tyr Asp Asp
            330             335             340

CAG GTC GGC AAA GTC TCC CTC GTG GGT GCT GGC ATG AAG TCT CAC CCA     1290
Gln Val Gly Lys Val Ser Leu Val Gly Ala Gly Met Lys Ser His Pro
        345             350             355

GGT GTT ACC GCA GAG TTC ATG GAA GCT CTG CGC GAT GTC AAC GTG AAC     1338
Gly Val Thr Ala Glu Phe Met Glu Ala Leu Arg Asp Val Asn Val Asn
```

```
            360                 365                 370
ATC GAA TTG ATT TCC ACC TCT GAG ATC CGC ATT TCC GTG CTG ATC CGT    1386
Ile Glu Leu Ile Ser Thr Ser Glu Ile Arg Ile Ser Val Leu Ile Arg
375                 380                 385                 390

GAA GAT GAT CTG GAT GCT GCT GCA CGT GCA TTG CAT GAG CAG TTC CAG    1434
Glu Asp Asp Leu Asp Ala Ala Ala Arg Ala Leu His Glu Gln Phe Gln
                395                 400                 405

CTG GGC GGC GAA GAC GAA GCC GTC GTT TAT GCA GGC ACC GGA CGC TAA    1482
Leu Gly Gly Glu Asp Glu Ala Val Val Tyr Ala Gly Thr Gly Arg
            410                 415                 420

AGTTTTAAAG GAGTAGTTTT ACAATGACCA CCATCGCAGT TGTTGGTGCA ACCGGCCAGG  1542

TCGGCCAGGT TATGCGCACC CTTTTGGAAG AGCGCAATTT CCCAGCTGAC ACTGTTCGTT  1602

TCTTTGCTTC CCCGCGTTCC GCAGGCCGTA AGATTGAATT C                     1643

(2) INFORMATION FOR SEQ ID NO:5:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO: 5:

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255
```

```
Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

(2) INFORMATION FOR SEQ ID NO:6:

(i) SEQUENCE CHARACTERISTICS:
        (A) LENGTH: 1643 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
         (A) ORGANISM: Brevibacterium lactofermentum
         (B) STRAIN: ATCC 13869

(ix) FEATURE:
         (A) NAME/KEY: CDS
         (B) LOCATION: 964..1482

(xi) SEQUENCE DESCRIPTION: SEQ ID NO: 6:

TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAGGTGG CCCTGGTCGT ACAGAAATAT     240

GGCGGTTCCT CGCTTGAGAG TGCGGAACGC ATTAGAAACG TCGCTGAACG GATCGTTGCC     300

ACCAAGAAGG CTGGAAATGA TGTCGTGGTT GTCTGCTCCG CAATGGGAGA CACCACGGAT     360

GAACTTCTAG AACTTGCAGC GGCAGTGAAT CCCGTTCCGC CAGCTCGTGA AATGGATATG     420

CTCCTGACTG CTGGTGAGCG TATTTCTAAC GCTCTCGTCG CCATGGCTAT TGAGTCCCTT     480

GGCGCAGAAG CTCAATCTTT CACTGGCTCT CAGGCTGGTG TGCTCACCAC CGAGCGCCAC     540

GGAAACGCAC GCATTGTTGA CGTCACACCG GGTCGTGTGC GTGAAGCACT CGATGAGGGC     600

AAGATCTGCA TTGTTGCTGG TTTTCAGGGT GTTAATAAAG AAACCCGCGA TGTCACCACG     660

TTGGGTCGTG GTGGTTCTGA CACCACTGCA GTTGCGTTGG CAGCTGCTTT GAACGCTGAT     720
```

-continued

```
GTGTGTGAGA TTTACTCGGA CGTTGACGGT GTGTATACCG CTGACCCGCG CATCGTTCCT      780

AATGCACAGA AGCTGGAAAA GCTCAGCTTC GAAGAAATGC TGGAACTTGC TGCTGTTGGC      840

TCCAAGATTT TGGTGCTGCG CAGTGTTGAA TACGCTCGTG CATTCAATGT GCCACTTCGC      900

GTACGCTCGT CTTATAGTAA TGATCCCGGC ACTTTGATTG CCGGCTCTAT GGAGGATATT      960

CCT GTG GAA GAA GCA GTC CTT ACC GGT GTC GCA ACC GAC AAG TCC GAA       1008
    Met Glu Glu Ala Val Leu Thr Gly Val Ala Thr Asp Lys Ser Glu
    1               5                   10                  15

GCC AAA GTA ACC GTT CTG GGT ATT TCC GAT AAG CCA GGC GAG GCT GCC       1056
Ala Lys Val Thr Val Leu Gly Ile Ser Asp Lys Pro Gly Glu Ala Ala
            20                  25                  30

AAG GTT TTC CGT GCG TTG GCT GAT GCA GAA ATC AAC ATT GAC ATG GTT       1104
Lys Val Phe Arg Ala Leu Ala Asp Ala Glu Ile Asn Ile Asp Met Val
                35                  40                  45

CTG CAG AAC GTC TCC TCT GTG GAA GAC GGC ACC ACC GAC ATC ACG TTC       1152
Leu Gln Asn Val Ser Ser Val Glu Asp Gly Thr Thr Asp Ile Thr Phe
        50                  55                  60

ACC TGC CCT CGC GCT GAC GGA CGC CGT GCG ATG GAG ATC TTG AAG AAG       1200
Thr Cys Pro Arg Ala Asp Gly Arg Arg Ala Met Glu Ile Leu Lys Lys
65                  70                  75

CTT CAG GTT CAG GGC AAC TGG ACC AAT GTG CTT TAC GAC GAC CAG GTC       1248
Leu Gln Val Gln Gly Asn Trp Thr Asn Val Leu Tyr Asp Asp Gln Val
80                  85                  90                  95

GGC AAA GTC TCC CTC GTG GGT GCT GGC ATG AAG TCT CAC CCA GGT GTT       1296
Gly Lys Val Ser Leu Val Gly Ala Gly Met Lys Ser His Pro Gly Val
                100                 105                 110

ACC GCA GAG TTC ATG GAA GCT CTG CGC GAT GTC AAC GTG AAC ATC GAA       1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT       1392
Leu Ile Ser Thr Ser Glu Ile Arg Ile Ser Val Leu Ile Arg Glu Asp
        130                 135                 140

GAT CTG GAT GCT GCT GCA CGT GCA TTG CAT GAG CAG TTC CAG CTG GGC       1440
Asp Leu Asp Ala Ala Ala Arg Ala Leu His Glu Gln Phe Gln Leu Gly
145                 150                 155

GGC GAA GAC GAA GCC GTC GTT TAT GCA GGC ACC GGA CGC TAAAGTTTTAA      1490
Gly Glu Asp Glu Ala Val Val Tyr Ala Gly Thr Gly Arg
160                 165                 170

AGGAGTAGTT TTACAATGAC CACCATCGCA GTTGTTGGTG CAACCGGCCA GGTCGGCCAG     1550

GTTATGCGCA CCCTTTTGGA AGAGCGCAAT TTCCCAGCTG ACACTGTTCG TTTCTTTGCT     1610

TCCCCGCGTT CCGCAGGCCG TAAGATTGAA TTC                                  1643
```

(2) INFORMATION FOR SEQ ID NO:7:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Glu Glu Ala Val Leu Thr Gly Val Ala Thr Asp Lys Ser Glu Ala
1               5                   10                  15

Lys Val Thr Val Leu Gly Ile Ser Asp Lys Pro Gly Glu Ala Ala Lys
            20                  25                  30

Val Phe Arg Ala Leu Ala Asp Ala Glu Ile Asn Ile Asp Met Val Leu
        35                  40                  45
```

```
Gln Asn Val Ser Ser Val Glu Asp Gly Thr Thr Asp Ile Thr Phe Thr
         50                  55                  60

Cys Pro Arg Ala Asp Gly Arg Arg Ala Met Glu Ile Leu Lys Lys Leu
 65                  70                  75                  80

Gln Val Gln Gly Asn Trp Thr Asn Val Leu Tyr Asp Asp Gln Val Gly
                 85                  90                  95

Lys Val Ser Leu Val Gly Ala Gly Met Lys Ser His Pro Gly Val Thr
            100                 105                 110

Ala Glu Phe Met Glu Ala Leu Arg Asp Val Asn Val Asn Ile Glu Leu
            115                 120                 125

Ile Ser Thr Ser Glu Ile Arg Ile Ser Val Leu Ile Arg Glu Asp Asp
        130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
                165                 170
```

(2) INFORMATION FOR SEQ ID NO:8:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: no (xi) SEQUENCE DESCRIPTION: SEQ ID NO: 8:

GTGGAGCCGA CCATTCCGCG AGG                                23

(2) INFORMATION FOR SEQ ID NO:9:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: yes (xi) SEQUENCE DESCRIPTION: SEQ ID NO: 9:

CCAAAACCGC CCTCCACGGC GAA                                23

(2) INFORMATION FOR SEQ ID NO:10:

(i) SEQUENCE CHARACTERISTICS:
        (A) LENGTH: 3579 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 533..2182

(ix) FEATURE:
   (A) NAME/KEY: CDS
   (B) LOCATION: 2188..3522

(xi) SEQUENCE DESCRIPTION: SEQ ID NO: 10:

```
GTGGAGCCGA CCATTCCGCG AGGCTGCACT GCAACGAGGT CGTAGTTTTG GTACATGGCT      60

TCTGGCCAGT TCATGGATTG GCTGCCGAAG AAGCTATAGG CATCGCACCA GGGCCACCGA     120

GTTACCGAAG ATGGTGCCGT GCTTTTCGCC TTGGGCAGGG ACCTTGACAA AGCCCACGCT     180

GATATCGCCA AGTGAGGGAT CAGAATAGTG CATGGGCACG TCGATGCTGC CACATTGAGC     240

GGAGGCAATA TCTACCTGAG GTGGGCATTC TTCCCAGCGG ATGTTTTCTT GCGCTGCTGC     300

AGTGGGCATT GATACCAAAA AGGGGCTAAG CGCAGTCGAG GCGGCAAGAA CTGCTACTAC     360

CCTTTTTATT GTCGAACGGG GCATTACGGC TCCAAGGACG TTTGTTTTCT GGGTCAGTTA     420

CCCCAAAAAG CATATACAGA GACCAATGAT TTTTCATTAA AAAGGCAGGG ATTTGTTATA     480

AGTATGGGTC GTATTCTGTG CGACGGGTGT ACCTCGGCTA GAATTTCTCC CC ATG         535
                                                            Met
                                                            1
```

```
ACA CCA GCT GAT CTC GCA ACA TTG ATT AAA GAG ACC GCG GTA GAG GTT      583
Thr Pro Ala Asp Leu Ala Thr Leu Ile Lys Glu Thr Ala Val Glu Val
            5                  10                  15

TTG ACC TCC CGC GAG CTC GAT ACT TCT GTT CTT CCG GAG CAG GTA GTT      631
Leu Thr Ser Arg Glu Leu Asp Thr Ser Val Leu Pro Glu Gln Val Val
        20                  25                  30

GTG GAG CGT CCG CGT AAC CCA GAG CAC GGC GAT TAC GCC ACC AAC ATT      679
Val Glu Arg Pro Arg Asn Pro Glu His Gly Asp Tyr Ala Thr Asn Ile
    35                  40                  45

GCA TTG CAG GTG GCT AAA AAG GTC GGT CAG AAC CCT CGG GAT TTG GCT      727
Ala Leu Gln Val Ala Lys Lys Val Gly Gln Asn Pro Arg Asp Leu Ala
50                  55                  60                  65

ACC TGG CTG GCA GAG GCA TTG GCT GCA GAT GAC GCC ATT GAT TCT GCT      775
Thr Trp Leu Ala Glu Ala Leu Ala Ala Asp Asp Ala Ile Asp Ser Ala
                70                  75                  80

GAA ATT GCT GGC CCA GGC TTT TTG AAC ATT CGC CTT GCT GCA GCA GCA      823
Glu Ile Ala Gly Pro Gly Phe Leu Asn Ile Arg Leu Ala Ala Ala Ala
            85                  90                  95

CAG GGT GAA ATT GTG GCC AAG ATT CTG GCA CAG GGC GAG ACT TTC GGA      871
Gln Gly Glu Ile Val Ala Lys Ile Leu Ala Gln Gly Glu Thr Phe Gly
        100                 105                 110

AAC TCC GAT CAC CTT TCC CAC TTG GAC GTG AAC CTC GAG TTC GTT TCT      919
Asn Ser Asp His Leu Ser His Leu Asp Val Asn Leu Glu Phe Val Ser
    115                 120                 125

GCA AAC CCA ACC GGA CCT ATT CAC CTT GGC GGA ACC CGC TGG GCT GCC      967
Ala Asn Pro Thr Gly Pro Ile His Leu Gly Gly Thr Arg Trp Ala Ala
130                 135                 140                 145

GTG GGT GAC TCT TTG GGT CGT GTG CTG GAG GCT TCC GGC GCG AAA GTG     1015
Val Gly Asp Ser Leu Gly Arg Val Leu Glu Ala Ser Gly Ala Lys Val
                150                 155                 160

ACC CGC GAA TAC TAC TTC AAC GAT CAC GGT CGC CAG ATC GAT CGT TTC     1063
Thr Arg Glu Tyr Tyr Phe Asn Asp His Gly Arg Gln Ile Asp Arg Phe
            165                 170                 175

GCT TTG TCC CTT CTT GCA GCG GCG AAG GGC GAG CCA ACG CCA GAA GAC     1111
Ala Leu Ser Leu Leu Ala Ala Ala Lys Gly Glu Pro Thr Pro Glu Asp
        180                 185                 190

GGT TAT GGC GGC GAA TAC ATT AAG GAA ATT GCG GAG GCA ATC GTC GAA     1159
Gly Tyr Gly Gly Glu Tyr Ile Lys Glu Ile Ala Glu Ala Ile Val Glu
    195                 200                 205

AAG CAT CCT GAA GCG TTG GCT TTG GAG CCT GCC GCA ACC CAG GAG CTT     1207
```

```
Lys His Pro Glu Ala Leu Ala Leu Glu Pro Ala Ala Thr Gln Glu Leu
210                 215                 220                 225

TTC CGC GCT GAA GGC GTG GAG ATG ATG TTC GAG CAC ATC AAA TCT TCC      1255
Phe Arg Ala Glu Gly Val Glu Met Met Phe Glu His Ile Lys Ser Ser
                    230                 235                 240

CTG CAT GAG TTC GGC ACC GAT TTC GAT GTC TAC TAC CAC GAG AAC TCC      1303
Leu His Glu Phe Gly Thr Asp Phe Asp Val Tyr Tyr His Glu Asn Ser
                245                 250                 255

CTG TTC GAG TCC GGT GCG GTG GAC AAG GCC GTG CAG GTG CTG AAG GAC      1351
Leu Phe Glu Ser Gly Ala Val Asp Lys Ala Val Gln Val Leu Lys Asp
            260                 265                 270

AAC GGC AAC CTG TAC GAA AAC GAG GGC GCT TGG TGG CTG CGT TCC ACC      1399
Asn Gly Asn Leu Tyr Glu Asn Glu Gly Ala Trp Trp Leu Arg Ser Thr
        275                 280                 285

GAA TTC GGC GAT GAC AAA GAC CGC GTG GTG ATC AAG TCT GAC GGC GAC      1447
Glu Phe Gly Asp Asp Lys Asp Arg Val Val Ile Lys Ser Asp Gly Asp
290                 295                 300                 305

GCA GCC TAC ATC GCT GGC GAT ATC GCG TAC GTG GCT GAT AAG TTC TCC      1495
Ala Ala Tyr Ile Ala Gly Asp Ile Ala Tyr Val Ala Asp Lys Phe Ser
                    310                 315                 320

CGC GGA CAC AAC CTA AAC ATC TAC ATG TTG GGT GCT GAC CAC CAT GGT      1543
Arg Gly His Asn Leu Asn Ile Tyr Met Leu Gly Ala Asp His His Gly
                325                 330                 335

TAC ATC GCG CGC CTG AAG GCA GCG GCG GCG GCA CTT GGC TAC AAG CCA      1591
Tyr Ile Ala Arg Leu Lys Ala Ala Ala Ala Ala Leu Gly Tyr Lys Pro
            340                 345                 350

GAA GGC GTT GAA GTC CTG ATT GGC CAG ATG GTG AAC CTG CTT CGC GAC      1639
Glu Gly Val Glu Val Leu Ile Gly Gln Met Val Asn Leu Leu Arg Asp
        355                 360                 365

GGC AAG GCA GTG CGT ATG TCC AAG CGT GCA GGC ACC GTG GTC ACC CTA      1687
Gly Lys Ala Val Arg Met Ser Lys Arg Ala Gly Thr Val Val Thr Leu
370                 375                 380                 385

GAT GAC CTC GTT GAA GCA ATC GGC ATC GAT GCG GCG CGT TAC TCC CTG      1735
Asp Asp Leu Val Glu Ala Ile Gly Ile Asp Ala Ala Arg Tyr Ser Leu
                    390                 395                 400

ATC CGT TCC TCC GTG GAT TCT TCC CTG GAT ATC GAT CTC GGC CTG TGG      1783
Ile Arg Ser Ser Val Asp Ser Ser Leu Asp Ile Asp Leu Gly Leu Trp
                405                 410                 415

GAA TCC CAG TCC TCC GAC AAC CCT GTG TAC TAC GTG CAG TAC GGA CAC      1831
Glu Ser Gln Ser Ser Asp Asn Pro Val Tyr Tyr Val Gln Tyr Gly His
            420                 425                 430

GCT CGT CTG TGC TCC ATC GCG CGC AAG GCA GAG ACC TTG GGT GTC ACC      1879
Ala Arg Leu Cys Ser Ile Ala Arg Lys Ala Glu Thr Leu Gly Val Thr
        435                 440                 445

GAG GAA GGC GCA GAC CTA TCT CTA CTG ACC CAC GAC CGC GAA GGC GAT      1927
Glu Glu Gly Ala Asp Leu Ser Leu Leu Thr His Asp Arg Glu Gly Asp
450                 455                 460                 465

CTC ATC CGC ACA CTC GGA GAG TTC CCA GCA GTG GTG AAG GCT GCC GCT      1975
Leu Ile Arg Thr Leu Gly Glu Phe Pro Ala Val Val Lys Ala Ala Ala
                    470                 475                 480

GAC CTA CGT GAA CCA CAC CGC ATT GCC CGC TAT GCT GAG GAA TTA GCT      2023
Asp Leu Arg Glu Pro His Arg Ile Ala Arg Tyr Ala Glu Glu Leu Ala
                485                 490                 495

GGA ACT TTC CAC CGC TTC TAC GAT TCC TGC CAC ATC CTT CCA AAG GTT      2071
Gly Thr Phe His Arg Phe Tyr Asp Ser Cys His Ile Leu Pro Lys Val
            500                 505                 510

GAT GAG GAT ACG GCA CCA ATC CAC ACA GCA CGT CTG GCA CTT GCA GCA      2119
Asp Glu Asp Thr Ala Pro Ile His Thr Ala Arg Leu Ala Leu Ala Ala
        515                 520                 525
```

```
GCA ACC CGC CAG ACC CTC GCT AAC GCC CTG CAC CTG GTT GGC GTT TCC       2167
Ala Thr Arg Gln Thr Leu Ala Asn Ala Leu His Leu Val Gly Val Ser
530                 535                 540                 545

GCA CCG GAG AAG ATG TAACA ATG GCT ACA GTT GAA AAT TTC AAT GAA          2214
Ala Pro Glu Lys Met       Met Ala Thr Val Glu Asn Phe Asn Glu
                550         1               5

CTT CCC GCA CAC GTA TGG CCA CGC AAT GCC GTG CGC CAA GAA GAC GGC       2262
Leu Pro Ala His Val Trp Pro Arg Asn Ala Val Arg Gln Glu Asp Gly
 10              15                  20                  25

GTT GTC ACC GTC GCT GGT GTG CCT CTG CCT GAC CTC GCT GAA GAA TAC       2310
Val Val Thr Val Ala Gly Val Pro Leu Pro Asp Leu Ala Glu Glu Tyr
                 30                  35                  40

GGA ACC CCA CTG TTC GTA GTC GAC GAG GAC GAT TTC CGT TCC CGC TGT       2358
Gly Thr Pro Leu Phe Val Val Asp Glu Asp Asp Phe Arg Ser Arg Cys
             45                  50                  55

CGC GAC ATG GCT ACC GCA TTC GGT GGA CCA GGC AAT GTG CAC TAC GCA       2406
Arg Asp Met Ala Thr Ala Phe Gly Gly Pro Gly Asn Val His Tyr Ala
         60                  65                  70

TCT AAA GCG TTC CTG ACC AAG ACC ATT GCA CGT TGG GTT GAT GAA GAG       2454
Ser Lys Ala Phe Leu Thr Lys Thr Ile Ala Arg Trp Val Asp Glu Glu
 75                  80                  85

GGG CTG GCA CTG GAC ATT GCA TCC ATC AAC GAA CTG GGC ATT GCC CTG       2502
Gly Leu Ala Leu Asp Ile Ala Ser Ile Asn Glu Leu Gly Ile Ala Leu
 90                  95                 100                 105

GCC GCT GGT TTC CCC GCC AGC CGT ATC ACC GCG CAC GGC AAC AAC AAA       2550
Ala Ala Gly Phe Pro Ala Ser Arg Ile Thr Ala His Gly Asn Asn Lys
                110                 115                 120

GGC GTA GAG TTC CTG CGC GCG TTG GTT CAA AAC GGT GTG GGA CAC GTG       2598
Gly Val Glu Phe Leu Arg Ala Leu Val Gln Asn Gly Val Gly His Val
                125                 130                 135

GTG CTG GAC TCC GCA CAG GAA CTA GAA CTG TTG GAT TAC GTT GCC GCT       2646
Val Leu Asp Ser Ala Gln Glu Leu Glu Leu Leu Asp Tyr Val Ala Ala
140                 145                 150

GGT GAA GGC AAG ATT CAG GAC GTG TTG ATC CGC GTA AAG CCA GGC ATC       2694
Gly Glu Gly Lys Ile Gln Asp Val Leu Ile Arg Val Lys Pro Gly Ile
155                 160                 165

GAA GCA CAC ACC CAC GAG TTC ATC GCC ACT AGC CAC GAA GAC CAG AAG       2742
Glu Ala His Thr His Glu Phe Ile Ala Thr Ser His Glu Asp Gln Lys
170                 175                 180                 185

TTC GGA TTC TCC CTG GCA TCC GGT TCC GCA TTC GAA GCA GCA AAA GCC       2790
Phe Gly Phe Ser Leu Ala Ser Gly Ser Ala Phe Glu Ala Ala Lys Ala
                190                 195                 200

GCC AAC AAC GCA GAA AAC CTG AAC CTG GTT GGC CTG CAC TGC CAC GTT       2838
Ala Asn Asn Ala Glu Asn Leu Asn Leu Val Gly Leu His Cys His Val
                205                 210                 215

GGT TCC CAG GTG TTC GAC GCC GAA GGC TTC AAG CTG GCA GCA GAA CGC       2886
Gly Ser Gln Val Phe Asp Ala Glu Gly Phe Lys Leu Ala Ala Glu Arg
                220                 225                 230

GTG TTG GGC CTG TAC TCA CAG ATC CAC AGC GAA CTG GGC GTT GCC CTT       2934
Val Leu Gly Leu Tyr Ser Gln Ile His Ser Glu Leu Gly Val Ala Leu
235                 240                 245

CCT GAA CTG GAT CTC GGT GGC GGA TAC GGC ATT GCC TAT ACC GCA GCT       2982
Pro Glu Leu Asp Leu Gly Gly Gly Tyr Gly Ile Ala Tyr Thr Ala Ala
250                 255                 260                 265

GAA GAA CCA CTC AAC GTC GCA GAA GTT GCC TCC GAC CTG CTC ACC GCA       3030
Glu Glu Pro Leu Asn Val Ala Glu Val Ala Ser Asp Leu Leu Thr Ala
                270                 275                 280

GTC GGA AAA ATG GCA GCG GAA CTA GGC ATC GAC GCA CCA ACC GTG CTT       3078
Val Gly Lys Met Ala Ala Glu Leu Gly Ile Asp Ala Pro Thr Val Leu
                285                 290                 295
```

```
GTT GAG CCC GGC CGC GCT ATC GCA GGC CCC TCC ACC GTG ACC ATC TAC    3126
Val Glu Pro Gly Arg Ala Ile Ala Gly Pro Ser Thr Val Thr Ile Tyr
        300                 305                 310

GAA GTC GGC ACC ACC AAA GAC GTC CAC GTA GAC GAC GAC AAA ACC CGC    3174
Glu Val Gly Thr Thr Lys Asp Val His Val Asp Asp Asp Lys Thr Arg
        315                 320                 325

CGT TAC ATC GCC GTG GAC GGA GGC ATG TCC GAC AAC ATC CGC CCA GCA    3222
Arg Tyr Ile Ala Val Asp Gly Gly Met Ser Asp Asn Ile Arg Pro Ala
330                 335                 340                 345

CTC TAC GGC TCC GAA TAC GAC GCC CGC GTA GTA TCC CGC TTC GCC GAA    3270
Leu Tyr Gly Ser Glu Tyr Asp Ala Arg Val Val Ser Arg Phe Ala Glu
                350                 355                 360

GGA GAC CCA GTA AGC ACC CGC ATC GTG GGC TCC CAC TGC GAA TCC GGC    3318
Gly Asp Pro Val Ser Thr Arg Ile Val Gly Ser His Cys Glu Ser Gly
            365                 370                 375

GAT ATC CTG ATC AAC GAT GAA ATC TAC CCA TCT GAC ATC ACC AGC GGC    3366
Asp Ile Leu Ile Asn Asp Glu Ile Tyr Pro Ser Asp Ile Thr Ser Gly
        380                 385                 390

GAC TTC CTT GCA CTC GCA GCC ACC GGC GCA TAC TGC TAC GCC ATG AGC    3414
Asp Phe Leu Ala Leu Ala Ala Thr Gly Ala Tyr Cys Tyr Ala Met Ser
    395                 400                 405

TCC CGC TAC AAC GCC TTC ACA CGG CCC GCC GTC GTG TCC GTC CGC GCT    3462
Ser Arg Tyr Asn Ala Phe Thr Arg Pro Ala Val Val Ser Val Arg Ala
410                 415                 420                 425

GGC AGC TCC CGC CTC ATG CTG CGC CGC GAA ACG CTC GAC GAC ATC CTC    3510
Gly Ser Ser Arg Leu Met Leu Arg Arg Glu Thr Leu Asp Asp Ile Leu
                430                 435                 440

TCA CTA GAG GCA TAACGCTTTT CGACGCCTGA CCCCGCCCTT CACCTTCGCC        3562
Ser Leu Glu Ala
            445

GTGGAGGGCG GTTTTGG                                                 3579

(2) INFORMATION FOR SEQ ID NO:11:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO: 11:

Met Thr Pro Ala Asp Leu Ala Thr Leu Ile Lys Glu Thr Ala Val Glu
 1               5                  10                  15

Val Leu Thr Ser Arg Glu Leu Asp Thr Ser Val Leu Pro Glu Gln Val
            20                  25                  30

Val Val Glu Arg Pro Arg Asn Pro Glu His Gly Asp Tyr Ala Thr Asn
        35                  40                  45

Ile Ala Leu Gln Val Ala Lys Lys Val Gly Gln Asn Pro Arg Asp Leu
    50                  55                  60

Ala Thr Trp Leu Ala Glu Ala Leu Ala Ala Asp Asp Ala Ile Asp Ser
65                  70                  75                  80

Ala Glu Ile Ala Gly Pro Gly Phe Leu Asn Ile Arg Leu Ala Ala Ala
                85                  90                  95

Ala Gln Gly Glu Ile Val Ala Lys Ile Leu Ala Gln Gly Glu Thr Phe
            100                 105                 110

Gly Asn Ser Asp His Leu Ser His Leu Asp Val Asn Leu Glu Phe Val
        115                 120                 125
```

-continued

```
Ser Ala Asn Pro Thr Gly Pro Ile His Leu Gly Gly Thr Arg Trp Ala
    130                 135                 140

Ala Val Gly Asp Ser Leu Gly Arg Val Leu Glu Ala Ser Gly Ala Lys
145                 150                 155                 160

Val Thr Arg Glu Tyr Tyr Phe Asn Asp His Gly Arg Gln Ile Asp Arg
                165                 170                 175

Phe Ala Leu Ser Leu Leu Ala Ala Ala Lys Gly Glu Pro Thr Pro Glu
            180                 185                 190

Asp Gly Tyr Gly Gly Glu Tyr Ile Lys Glu Ile Ala Glu Ala Ile Val
        195                 200                 205

Glu Lys His Pro Glu Ala Leu Ala Leu Glu Pro Ala Ala Thr Gln Glu
    210                 215                 220

Leu Phe Arg Ala Glu Gly Val Glu Met Met Phe Glu His Ile Lys Ser
225                 230                 235                 240

Ser Leu His Glu Phe Gly Thr Asp Phe Asp Val Tyr Tyr His Glu Asn
                245                 250                 255

Ser Leu Phe Glu Ser Gly Ala Val Asp Lys Ala Val Gln Val Leu Lys
            260                 265                 270

Asp Asn Gly Asn Leu Tyr Glu Asn Glu Gly Ala Trp Trp Leu Arg Ser
        275                 280                 285

Thr Glu Phe Gly Asp Asp Lys Asp Arg Val Val Ile Lys Ser Asp Gly
    290                 295                 300

Asp Ala Ala Tyr Ile Ala Gly Asp Ile Ala Tyr Val Ala Asp Lys Phe
305                 310                 315                 320

Ser Arg Gly His Asn Leu Asn Ile Tyr Met Leu Gly Ala Asp His His
                325                 330                 335

Gly Tyr Ile Ala Arg Leu Lys Ala Ala Ala Ala Leu Gly Tyr Lys
            340                 345                 350

Pro Glu Gly Val Glu Val Leu Ile Gly Gln Met Val Asn Leu Leu Arg
        355                 360                 365

Asp Gly Lys Ala Val Arg Met Ser Lys Arg Ala Gly Thr Val Val Thr
    370                 375                 380

Leu Asp Asp Leu Val Glu Ala Ile Gly Ile Asp Ala Ala Arg Tyr Ser
385                 390                 395                 400

Leu Ile Arg Ser Ser Val Asp Ser Ser Leu Asp Ile Asp Leu Gly Leu
                405                 410                 415

Trp Glu Ser Gln Ser Ser Asp Asn Pro Val Tyr Tyr Val Gln Tyr Gly
            420                 425                 430

His Ala Arg Leu Cys Ser Ile Ala Arg Lys Ala Glu Thr Leu Gly Val
        435                 440                 445

Thr Glu Glu Gly Ala Asp Leu Ser Leu Leu Thr His Asp Arg Glu Gly
    450                 455                 460

Asp Leu Ile Arg Thr Leu Gly Glu Phe Pro Ala Val Val Lys Ala Ala
465                 470                 475                 480

Ala Asp Leu Arg Glu Pro His Arg Ile Ala Arg Tyr Ala Glu Glu Leu
                485                 490                 495

Ala Gly Thr Phe His Arg Phe Tyr Asp Ser Cys His Ile Leu Pro Lys
            500                 505                 510

Val Asp Glu Asp Thr Ala Pro Ile His Thr Ala Arg Leu Ala Leu Ala
        515                 520                 525

Ala Ala Thr Arg Gln Thr Leu Ala Asn Ala Leu His Leu Val Gly Val
    530                 535                 540

Ser Ala Pro Glu Lys Met
```

545            550

(2) INFORMATION FOR SEQ ID NO:12:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 12:

Met Ala Thr Val Glu Asn Phe Asn Glu Leu Pro Ala His Val Trp Pro
 1               5                  10                  15

Arg Asn Ala Val Arg Gln Glu Asp Gly Val Val Thr Val Ala Gly Val
            20                  25                  30

Pro Leu Pro Asp Leu Ala Glu Glu Tyr Gly Thr Pro Leu Phe Val Val
        35                  40                  45

Asp Glu Asp Asp Phe Arg Ser Arg Cys Arg Asp Met Ala Thr Ala Phe
    50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Gly Leu Ala Leu Asp Ile Ala
                85                  90                  95

Ser Ile Asn Glu Leu Gly Ile Ala Leu Ala Ala Gly Phe Pro Ala Ser
                100                 105                 110

Arg Ile Thr Ala His Gly Asn Asn Lys Gly Val Glu Phe Leu Arg Ala
            115                 120                 125

Leu Val Gln Asn Gly Val Gly His Val Val Leu Asp Ser Ala Gln Glu
130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
                180                 185                 190

Gly Ser Ala Phe Glu Ala Ala Lys Ala Ala Asn Asn Ala Glu Asn Leu
            195                 200                 205

Asn Leu Val Gly Leu His Cys His Val Gly Ser Gln Val Phe Asp Ala
210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
275                 280                 285

Leu Gly Ile Asp Ala Pro Thr Val Leu Val Glu Pro Gly Arg Ala Ile
290                 295                 300

Ala Gly Pro Ser Thr Val Thr Ile Tyr Glu Val Gly Thr Thr Lys Asp
305                 310                 315                 320

Val His Val Asp Asp Asp Lys Thr Arg Arg Tyr Ile Ala Val Asp Gly
                325                 330                 335

Gly Met Ser Asp Asn Ile Arg Pro Ala Leu Tyr Gly Ser Glu Tyr Asp
            340                 345                 350

```
Ala Arg Val Val Ser Arg Phe Ala Glu Gly Asp Pro Val Ser Thr Arg
        355                 360                 365

Ile Val Gly Ser His Cys Glu Ser Gly Asp Ile Leu Ile Asn Asp Glu
        370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
        435                 440                 445
```

(2) INFORMATION FOR SEQ ID NO:13:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: no (xi) SEQUENCE DESCRIPTION: SEQ ID NO: 13:

```
TCGTCGGTCA GCCTGACGTC GAC                                       23
```

(2) INFORMATION FOR SEQ ID NO:14:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: yes (xi) SEQUENCE DESCRIPTION: SEQ ID NO: 14:

```
TCTTGGTGTCGAAAGTGCACACC                                         23
```

(2) INFORMATION FOR SEQ ID NO:15:

(i) SEQUENCE CHARACTERISTICS:
        (A) LENGTH: 3533 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 321..3077

(xi) SEQUENCE DESCRIPTION: SEQ ID NO: 15:

```
GGTGGTTCTG TTAAGGCAGA AACCGTCGCT GAGATCGTCG GTCAGCCTGA CGTCGACGGC   60

GGACTTGTCG GTGGCGCTTC CCTCGACGGT GAAGCATTCG CCAAGCTGGC TGCCAACGCT  120
```

```
GCGAGCGTTG CTTAAAGTAC AGAGCTTTAA AGCACAGCCT TAAAGCACAG CCTTAAAGCA         180

CAAGCACTGT AGAAGTGCGG TTTTGATGAG CCCATGAAAG CCATCGAAAT CAATCGCCCA         240

GCTAAACACC TGTTTTGCTG GGTGATTTTT TATCTCATGC ACGCCAACAC CCTCAATGTG         300

AAAGAGTGTT TAAAGTAGTT ATG ACT GAT TTT TTA CGC GAT GAC ATC AGG            350
                     Met Thr Asp Phe Leu Arg Asp Asp Ile Arg
                      1               5                  10

TTC CTC GGT CAA ATC CTC GGT GAG GTA ATT GCG GAA CAA GAA GGC CAG          398
Phe Leu Gly Gln Ile Leu Gly Glu Val Ile Ala Glu Gln Glu Gly Gln
                 15                  20                  25

GAG GTT TAT GAA CTG GTC GAA CAA GCG CGC CTG ACT TCT TTT GAT ATC          446
Glu Val Tyr Glu Leu Val Glu Gln Ala Arg Leu Thr Ser Phe Asp Ile
             30                  35                  40

GCC AAG GGC AAC GCC GAA ATG GAT AGC CTG GTT CAG GTT TTC GAC GGC          494
Ala Lys Gly Asn Ala Glu Met Asp Ser Leu Val Gln Val Phe Asp Gly
         45                  50                  55

ATT ACT CCA GCC AAG GCA ACA CCG ATT GCT CGC GCA TTT TCC CAC TTC          542
Ile Thr Pro Ala Lys Ala Thr Pro Ile Ala Arg Ala Phe Ser His Phe
     60                  65                  70

GCT CTG CTG GCT AAC CTG GCG GAA GAC CTC TAC GAT GAA GAG CTT CGT          590
Ala Leu Leu Ala Asn Leu Ala Glu Asp Leu Tyr Asp Glu Glu Leu Arg
 75                  80                  85                  90

GAA CAG GCT CTC GAT GCA GGC GAC ACC CCT CCG GAC AGC ACT CTT GAT          638
Glu Gln Ala Leu Asp Ala Gly Asp Thr Pro Pro Asp Ser Thr Leu Asp
                 95                 100                 105

GCC ACC TGG CTG AAA CTC AAT GAG GGC AAT GTT GGC GCA GAA GCT GTG          686
Ala Thr Trp Leu Lys Leu Asn Glu Gly Asn Val Gly Ala Glu Ala Val
             110                 115                 120

GCC GAT GTG CTG CGC AAT GCT GAG GTG GCG CCG GTT CTG ACT GCG CAC          734
Ala Asp Val Leu Arg Asn Ala Glu Val Ala Pro Val Leu Thr Ala His
         125                 130                 135

CCA ACT GAG ACT CGC CGC CGC ACT GTT TTT GAT GCG CAA AAG TGG ATC          782
Pro Thr Glu Thr Arg Arg Arg Thr Val Phe Asp Ala Gln Lys Trp Ile
     140                 145                 150

ACC ACC CAC ATG CGT GAA CGC CAC GCT TTG CAG TCT GCG GAG CCT ACC          830
Thr Thr His Met Arg Glu Arg His Ala Leu Gln Ser Ala Glu Pro Thr
155                 160                 165                 170

GCT CGT ACG CAA AGC AAG TTG GAT GAG ATC GAG AAG AAC ATC CGC CGT          878
Ala Arg Thr Gln Ser Lys Leu Asp Glu Ile Glu Lys Asn Ile Arg Arg
                 175                 180                 185

CGC ATC ACC ATT TTG TGG CAG ACC GCG TTG ATT CGT GTG GCC CGC CCA          926
Arg Ile Thr Ile Leu Trp Gln Thr Ala Leu Ile Arg Val Ala Arg Pro
             190                 195                 200

CGT ATC GAG GAC GAG ATC GAA GTA GGG CTG CGC TAC TAC AAG CTG AGC          974
Arg Ile Glu Asp Glu Ile Glu Val Gly Leu Arg Tyr Tyr Lys Leu Ser
         205                 210                 215

CTT TTG GAA GAG ATT CCA CGT ATC AAC CGT GAT GTG GCT GTT GAG CTT         1022
Leu Leu Glu Glu Ile Pro Arg Ile Asn Arg Asp Val Ala Val Glu Leu
     220                 225                 230

CGT GAG CGT TTC GGC GAG GAT GTT CCT TTG AAG CCC GTG GTC AAG CCA         1070
Arg Glu Arg Phe Gly Glu Asp Val Pro Leu Lys Pro Val Val Lys Pro
235                 240                 245                 250

GGT TCC TGG ATT GGT GGA GAC CAC GAC GGT AAC CCT TAT GTC ACC GCG         1118
Gly Ser Trp Ile Gly Gly Asp His Asp Gly Asn Pro Tyr Val Thr Ala
                 255                 260                 265

GAA ACA GTT GAG TAT TCC ACT CAC CGC GCT GCG GAA ACC GTG CTC AAG         1166
Glu Thr Val Glu Tyr Ser Thr His Arg Ala Ala Glu Thr Val Leu Lys
             270                 275                 280
```

```
TAC TAT GCA CGC CAG CTG CAT TCC CTC GAG CAT GAG CTC AGC CTG TCG      1214
Tyr Tyr Ala Arg Gln Leu His Ser Leu Glu His Glu Leu Ser Leu Ser
        285                 290                 295

GAC CGC ATG AAT AAG GTC ACC CCG CAG CTG CTT GCG CTG GCA GAT GCC      1262
Asp Arg Met Asn Lys Val Thr Pro Gln Leu Leu Ala Leu Ala Asp Ala
    300                 305                 310

GGG CAC AAC GAC GTG CCA AGC CGC GTG GAT GAG CCT TAT CGA CGC GCC      1310
Gly His Asn Asp Val Pro Ser Arg Val Asp Glu Pro Tyr Arg Arg Ala
315                 320                 325                 330

GTC CAT GGC GTT CGC GGA CGT ATC CTC GCG ACG ACG GCC GAG CTG ATC      1358
Val His Gly Val Arg Gly Arg Ile Leu Ala Thr Thr Ala Glu Leu Ile
                335                 340                 345

GGC GAG GAC GCC GTT GAG GGC GTG TGG TTC AAG GTC TTT ACT CCA TAC      1406
Gly Glu Asp Ala Val Glu Gly Val Trp Phe Lys Val Phe Thr Pro Tyr
            350                 355                 360

GCA TCT CCG GAA GAA TTC TTA AAC GAT GCG TTG ACC ATT GAT CAT TCT      1454
Ala Ser Pro Glu Glu Phe Leu Asn Asp Ala Leu Thr Ile Asp His Ser
        365                 370                 375

CTG CGT GAA TCC AAT GAC GTT CTC ATT GCC GAT GAT CGT TTG TCT GTG      1502
Leu Arg Glu Ser Asn Asp Val Leu Ile Ala Asp Asp Arg Leu Ser Val
    380                 385                 390

CTG ATT TCT GCC ATC GAG AGC TTT GGA TTC AAC CTT TAC GCA CTG GAT      1550
Leu Ile Ser Ala Ile Glu Ser Phe Gly Phe Asn Leu Tyr Ala Leu Asp
395                 400                 405                 410

CTG CGC CAA AAC TCC GAA AGC TAC GAG GAC GTC CTC ACC GAG CTT TTC      1598
Leu Arg Gln Asn Ser Glu Ser Tyr Glu Asp Val Leu Thr Glu Leu Phe
                415                 420                 425

GAA CGC GCC CAA GTC ACC GCA AAC TAC CGC GAG CTG TCT GAA GCA GAG      1646
Glu Arg Ala Gln Val Thr Ala Asn Tyr Arg Glu Leu Ser Glu Ala Glu
            430                 435                 440

AAG CTT GAG GTG CTG CTG AAG GAA CTG CGC AGC CCT CGT CCG CTG ATC      1694
Lys Leu Glu Val Leu Leu Lys Glu Leu Arg Ser Pro Arg Pro Leu Ile
        445                 450                 455

CCG CAC GGT TCA GAT GAA TAC AGC GAG GTC ACC GAC CGC GAG CTC GGC      1742
Pro His Gly Ser Asp Glu Tyr Ser Glu Val Thr Asp Arg Glu Leu Gly
    460                 465                 470

ATC TTC CGC ACC GCG TCG GAG GCT GTT AAG AAA TTC GGG CCA CGG ATG      1790
Ile Phe Arg Thr Ala Ser Glu Ala Val Lys Lys Phe Gly Pro Arg Met
475                 480                 485                 490

GTG CCT CAC TGC ATC ATC TCC ATG GCA TCA TCG GTC ACC GAT GTG CTC      1838
Val Pro His Cys Ile Ile Ser Met Ala Ser Ser Val Thr Asp Val Leu
                495                 500                 505

GAG CCG ATG GTA TTG CTC AAG GAA TTC GGC CTC ATT GCA GCC AAC GGC      1886
Glu Pro Met Val Leu Leu Lys Glu Phe Gly Leu Ile Ala Ala Asn Gly
            510                 515                 520

GAC AAC CCA CGC GGC ACC GTC GAT GTC ATC CCA CTG TTC GAA ACC ATC      1934
Asp Asn Pro Arg Gly Thr Val Asp Val Ile Pro Leu Phe Glu Thr Ile
        525                 530                 535

GAA GAT CTC CAG GCC GGC GCC GGA ATC CTC GAC GAA CTG TGG AAA ATT      1982
Glu Asp Leu Gln Ala Gly Ala Gly Ile Leu Asp Glu Leu Trp Lys Ile
    540                 545                 550

GAT CTT TAC CGC AAC TAC CTC CTG CAG CGC GAC AAC GTC CAG GAA GTC      2030
Asp Leu Tyr Arg Asn Tyr Leu Leu Gln Arg Asp Asn Val Gln Glu Val
555                 560                 565                 570

ATG CTC GGT TAC TCC GAT TCC AAC AAG GAT GGC GGA TAT TTC TCC GCA      2078
Met Leu Gly Tyr Ser Asp Ser Asn Lys Asp Gly Gly Tyr Phe Ser Ala
                575                 580                 585

AAC TGG GCG CTT TAC GAC GCG GAA CTG CAG CTC GTC GAA CTA TGC CGA      2126
Asn Trp Ala Leu Tyr Asp Ala Glu Leu Gln Leu Val Glu Leu Cys Arg
            590                 595                 600
```

-continued

```
TCA GCC GGG GTC AAG CTT CGC CTG TTC CAC GGC CGT GGT GGC ACC GTC      2174
Ser Ala Gly Val Lys Leu Arg Leu Phe His Gly Arg Gly Gly Thr Val
        605                 610                 615

GGC CGC GGT GGC GGA CCT TCC TAC GAC GCG ATT CTT GCC CAG CCC AGG      2222
Gly Arg Gly Gly Gly Pro Ser Tyr Asp Ala Ile Leu Ala Gln Pro Arg
    620                 625                 630

GGG GCT GTC CAA GGT TCC GTG CGC ATC ACC GAG CAG GGC GAG ATC ATC      2270
Gly Ala Val Gln Gly Ser Val Arg Ile Thr Glu Gln Gly Glu Ile Ile
635                 640                 645                 650

TCC GCT AAG TAC GGC AAC CCC GAA ACC GCG CGC CGA AAC CTC GAA GCT      2318
Ser Ala Lys Tyr Gly Asn Pro Glu Thr Ala Arg Arg Asn Leu Glu Ala
                655                 660                 665

CTG GTC TCA GCA ACG CTT GAG GCA TCG CTT CTC GAC GTC TCC GAA CTC      2366
Leu Val Ser Ala Thr Leu Glu Ala Ser Leu Leu Asp Val Ser Glu Leu
                    670                 675                 680

ACC GAT CAC CAA CGC GCG TAC GAC ATC ATG AGT GAG ATC TCT GAG CTC      2414
Thr Asp His Gln Arg Ala Tyr Asp Ile Met Ser Glu Ile Ser Glu Leu
                685                 690                 695

AGC TTG AAG AAG TAC GCC TCC TTG GTG CAC GAG GAT CAA GGC TTC ATC      2462
Ser Leu Lys Lys Tyr Ala Ser Leu Val His Glu Asp Gln Gly Phe Ile
    700                 705                 710

GAT TAC TTC ACC CAG TCC ACG CCG CTG CAG GAG ATT GGA TCC CTC AAC      2510
Asp Tyr Phe Thr Gln Ser Thr Pro Leu Gln Glu Ile Gly Ser Leu Asn
715                 720                 725                 730

ATC GGA TCC AGG CCT TCC TCA CGC AAG CAG ACC TCC TCG GTG GAA GAT      2558
Ile Gly Ser Arg Pro Ser Ser Arg Lys Gln Thr Ser Ser Val Glu Asp
                735                 740                 745

TTG CGA GCA ATC CCG TGG GTG CTC AGT TGG TCC CAG TCT CGT GTC ATG      2606
Leu Arg Ala Ile Pro Trp Val Leu Ser Trp Ser Gln Ser Arg Val Met
                750                 755                 760

CTG CCG GGC TGG TTT GGT GTC GGC ACC GCA CTT GAG CAA TGG ATT GGC      2654
Leu Pro Gly Trp Phe Gly Val Gly Thr Ala Leu Glu Gln Trp Ile Gly
    765                 770                 775

GAA GGG GAG CAG GCC ACC CAG CGC ATT GCC GAG CTA CAA ACA CTC AAC      2702
Glu Gly Glu Gln Ala Thr Gln Arg Ile Ala Glu Leu Gln Thr Leu Asn
    780                 785                 790

GAG TCC TGG CCA TTT TTC ACC TCA GTG TTG GAT AAC ATG GCT CAG GTG      2750
Glu Ser Trp Pro Phe Phe Thr Ser Val Leu Asp Asn Met Ala Gln Val
795                 800                 805                 810

ATG TCC AAG GCA GAG CTG CGT TTG GCA AAG CTC TAC GCA GAC CTG ATC      2798
Met Ser Lys Ala Glu Leu Arg Leu Ala Lys Leu Tyr Ala Asp Leu Ile
                815                 820                 825

CCA GAT AGG GAA GTA GCT GAG CGC GTT TAT GCC GTC ATC CGC GAG GAA      2846
Pro Asp Arg Glu Val Ala Glu Arg Val Tyr Ala Val Ile Arg Glu Glu
                830                 835                 840

TAC TTC CTG ACC AAG AAG ATG TTC TGC GTA ATC ACC GGT TCT GAT GAT      2894
Tyr Phe Leu Thr Lys Lys Met Phe Cys Val Ile Thr Gly Ser Asp Asp
                845                 850                 855

CTG CTT GAT GAC AAC CCG CTT CTC GCA CGA TCC GTC CAG CGC CGA TAC      2942
Leu Leu Asp Asp Asn Pro Leu Leu Ala Arg Ser Val Gln Arg Arg Tyr
    860                 865                 870

CCC TAC CTG CTT CCA CTC AAC GTG ATC CAG GTA GAG ATG ATG CGA CGC      2990
Pro Tyr Leu Leu Pro Leu Asn Val Ile Gln Val Glu Met Met Arg Arg
875                 880                 885                 890

TAC CGA AAA GGC GAC CAA AGC GAG CAA GTA TCC CGC AAC ATC CAG CTG      3038
Tyr Arg Lys Gly Asp Gln Ser Glu Gln Val Ser Arg Asn Ile Gln Leu
                895                 900                 905

ACC ATG AAC GGT CTT TCC ACT GCA CTG CGC AAC TCT GGC TAGTCCTGCT      3087
Thr Met Asn Gly Leu Ser Thr Ala Leu Arg Asn Ser Gly
```

-continued

```
          910              915
GGGTAGGTAG TACTCGTGTA TACTGTCTAA AGTTATTCGA AATCAGGTGG GAATAAGGTT    3147

CACCTGGGTT CTCAAACGGC AAAGGAACAT TTTCCACATG GCATTGACGC TTCAAATCAT    3207

CCTCGTCGTC GCCAGCCTGC TCATGACGGT TTTCGTCTTG CTGCACAAGG GCAAAGGCGG    3267

CGGACTCTCC AGCCTCTTCG GTGGCGGTGT GCAGTCCAAT CTTTCGGGCT CCACTGTTGT    3327

TGAAAAGAAC CTGGATCGCG TCACCATTTT GGTTGCCGTT ATCTGGATTG TGTGCATTGT    3387

CGCACTCAAC CTCATCCAGA CTTATTCATA AGACACGAGC TTAAAAAGAG CGGTTCCCTT    3447

TTCATAGGGG AGCCGCTTTT TTGGGTTTTG TCGACCTGTT GTCTCCCCAC TGTTCCTCGG    3507

TGTGCACTTT CGACACCAAG ATTTCG                                        3533
```

(2) INFORMATION FOR SEQ ID NO:16:

(i) SEQUENCE CHARACTERISTICS:
        (A) LENGTH: 919 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Thr Asp Phe Leu Arg Asp Asp Ile Arg Phe Leu Gly Gln Ile Leu
 1               5                  10                  15

Gly Glu Val Ile Ala Glu Gln Glu Gly Gln Glu Val Tyr Glu Leu Val
            20                  25                  30

Glu Gln Ala Arg Leu Thr Ser Phe Asp Ile Ala Lys Gly Asn Ala Glu
        35                  40                  45

Met Asp Ser Leu Val Gln Val Phe Asp Gly Ile Thr Pro Ala Lys Ala
    50                  55                  60

Thr Pro Ile Ala Arg Ala Phe Ser His Phe Ala Leu Leu Ala Asn Leu
65                  70                  75                  80

Ala Glu Asp Leu Tyr Asp Glu Glu Leu Arg Glu Gln Ala Leu Asp Ala
                85                  90                  95

Gly Asp Thr Pro Pro Asp Ser Thr Leu Asp Ala Thr Trp Leu Lys Leu
            100                 105                 110

Asn Glu Gly Asn Val Gly Ala Glu Ala Val Ala Asp Val Leu Arg Asn
        115                 120                 125

Ala Glu Val Ala Pro Val Leu Thr Ala His Pro Thr Glu Thr Arg Arg
    130                 135                 140

Arg Thr Val Phe Asp Ala Gln Lys Trp Ile Thr Thr His Met Arg Glu
145                 150                 155                 160

Arg His Ala Leu Gln Ser Ala Glu Pro Thr Ala Arg Thr Gln Ser Lys
                165                 170                 175

Leu Asp Glu Ile Glu Lys Asn Ile Arg Arg Ile Thr Ile Leu Trp
            180                 185                 190

Gln Thr Ala Leu Ile Arg Val Ala Arg Pro Ile Glu Asp Glu Ile
        195                 200                 205

Glu Val Gly Leu Arg Tyr Tyr Lys Leu Ser Leu Leu Glu Glu Ile Pro
    210                 215                 220

Arg Ile Asn Arg Asp Val Ala Val Glu Leu Arg Glu Arg Phe Gly Glu
225                 230                 235                 240

Asp Val Pro Leu Lys Pro Val Val Lys Pro Gly Ser Trp Ile Gly Gly
                245                 250                 255

Asp His Asp Gly Asn Pro Tyr Val Thr Ala Glu Thr Val Glu Tyr Ser
```

-continued

```
                260                 265                 270
Thr His Arg Ala Ala Glu Thr Val Leu Lys Tyr Tyr Ala Arg Gln Leu
            275                 280                 285

His Ser Leu Glu His Glu Leu Ser Leu Ser Asp Arg Met Asn Lys Val
            290                 295                 300

Thr Pro Gln Leu Leu Ala Leu Ala Asp Ala Gly His Asn Asp Val Pro
305                 310                 315                 320

Ser Arg Val Asp Glu Pro Tyr Arg Arg Ala Val His Gly Val Arg Gly
            325                 330                 335

Arg Ile Leu Ala Thr Thr Ala Glu Leu Ile Gly Glu Asp Ala Val Glu
            340                 345                 350

Gly Val Trp Phe Lys Val Phe Thr Pro Tyr Ala Ser Pro Glu Glu Phe
            355                 360                 365

Leu Asn Asp Ala Leu Thr Ile Asp His Ser Leu Arg Glu Ser Asn Asp
            370                 375                 380

Val Leu Ile Ala Asp Asp Arg Leu Ser Val Leu Ile Ser Ala Ile Glu
385                 390                 395                 400

Ser Phe Gly Phe Asn Leu Tyr Ala Leu Asp Leu Arg Gln Asn Ser Glu
            405                 410                 415

Ser Tyr Glu Asp Val Leu Thr Glu Leu Phe Glu Arg Ala Gln Val Thr
            420                 425                 430

Ala Asn Tyr Arg Glu Leu Ser Glu Ala Glu Lys Leu Glu Val Leu Leu
            435                 440                 445

Lys Glu Leu Arg Ser Pro Arg Pro Leu Ile Pro His Gly Ser Asp Glu
            450                 455                 460

Tyr Ser Glu Val Thr Asp Arg Glu Leu Gly Ile Phe Arg Thr Ala Ser
465                 470                 475                 480

Glu Ala Val Lys Lys Phe Gly Pro Arg Met Val Pro His Cys Ile Ile
            485                 490                 495

Ser Met Ala Ser Ser Val Thr Asp Val Leu Glu Pro Met Val Leu Leu
            500                 505                 510

Lys Glu Phe Gly Leu Ile Ala Ala Asn Gly Asp Asn Pro Arg Gly Thr
            515                 520                 525

Val Asp Val Ile Pro Leu Phe Glu Thr Ile Glu Asp Leu Gln Ala Gly
            530                 535                 540

Ala Gly Ile Leu Asp Glu Leu Trp Lys Ile Asp Leu Tyr Arg Asn Tyr
545                 550                 555                 560

Leu Leu Gln Arg Asp Asn Val Gln Glu Val Met Leu Gly Tyr Ser Asp
            565                 570                 575

Ser Asn Lys Asp Gly Gly Tyr Phe Ser Ala Asn Trp Ala Leu Tyr Asp
            580                 585                 590

Ala Glu Leu Gln Leu Val Glu Leu Cys Arg Ser Ala Gly Val Lys Leu
            595                 600                 605

Arg Leu Phe His Gly Arg Gly Gly Thr Val Gly Arg Gly Gly Gly Pro
            610                 615                 620

Ser Tyr Asp Ala Ile Leu Ala Gln Pro Arg Gly Ala Val Gln Gly Ser
625                 630                 635                 640

Val Arg Ile Thr Glu Gln Gly Glu Ile Ile Ser Ala Lys Tyr Gly Asn
            645                 650                 655

Pro Glu Thr Ala Arg Arg Asn Leu Glu Ala Leu Val Ser Ala Thr Leu
            660                 665                 670

Glu Ala Ser Leu Leu Asp Val Ser Glu Leu Thr Asp His Gln Arg Ala
            675                 680                 685
```

Tyr Asp Ile Met Ser Glu Ile Ser Glu Leu Ser Leu Lys Lys Tyr Ala
        690                 695                 700

Ser Leu Val His Glu Asp Gln Gly Phe Ile Asp Tyr Phe Thr Gln Ser
705                 710                 715                 720

Thr Pro Leu Gln Glu Ile Gly Ser Leu Asn Ile Gly Ser Arg Pro Ser
                725                 730                 735

Ser Arg Lys Gln Thr Ser Ser Val Glu Asp Leu Arg Ala Ile Pro Trp
            740                 745                 750

Val Leu Ser Trp Ser Gln Ser Arg Val Met Leu Pro Gly Trp Phe Gly
        755                 760                 765

Val Gly Thr Ala Leu Glu Gln Trp Ile Gly Glu Gly Glu Gln Ala Thr
770                 775                 780

Gln Arg Ile Ala Glu Leu Gln Thr Leu Asn Glu Ser Trp Pro Phe Phe
785                 790                 795                 800

Thr Ser Val Leu Asp Asn Met Ala Gln Val Met Ser Lys Ala Glu Leu
                805                 810                 815

Arg Leu Ala Lys Leu Tyr Ala Asp Leu Ile Pro Asp Arg Glu Val Ala
            820                 825                 830

Glu Arg Val Tyr Ala Val Ile Arg Glu Glu Tyr Phe Leu Thr Lys Lys
        835                 840                 845

Met Phe Cys Val Ile Thr Gly Ser Asp Asp Leu Leu Asp Asp Asn Pro
850                 855                 860

Leu Leu Ala Arg Ser Val Gln Arg Arg Tyr Pro Tyr Leu Leu Pro Leu
865                 870                 875                 880

Asn Val Ile Gln Val Glu Met Met Arg Arg Tyr Arg Lys Gly Asp Gln
                885                 890                 895

Ser Glu Gln Val Ser Arg Asn Ile Gln Leu Thr Met Asn Gly Leu Ser
            900                 905                 910

Thr Ala Leu Arg Asn Ser Gly
        915

(2) INFORMATION FOR SEQ ID NO:17:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: no (xi) SEQUENCE DESCRIPTION: SEQ ID NO: 17:

CGCGAGGTAC CACCTGTCAC                                                    20

(2) INFORMATION FOR SEQ ID NO:18:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: yes (xi) SEQUENCE DESCRIPTION: SEQ ID NO: 18:

-continued

```
CAATCCAGGT ACCGGCAACC                                              20

(2) INFORMATION FOR SEQ ID NO:19:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iv) ANTI-SENSE: no (xi) SEQUENCE DESCRIPTION: SEQ ID NO: 19:

GGATCCCCAA TCGATACCTG GAA                                          23

(2) INFORMATION FOR SEQ ID NO:20:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iv) ANTI-SENSE: yes (xi) SEQUENCE DESCRIPTION: SEQ ID NO: 20:

CGGTTCATCG CCAAGTTTTT CTT                                          23

(2) INFORMATION FOR SEQ ID NO:21:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iv) ANTI-SENSE: no (xi) SEQUENCE DESCRIPTION: SEQ ID NO: 21:

GTCGACGGAT CGCAAATGGC AAC                                          23

(2) INFORMATION FOR SEQ ID NO:22:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iv) ANTI-SENSE: yes (xi) SEQUENCE DESCRIPTION: SEQ ID NO: 22:

GGATCCTTGA GCACCTTGCG CAG                                          23

(2) INFORMATION FOR SEQ ID NO:23:

(i) SEQUENCE CHARACTERISTICS:
```

-continued

```
        (A) LENGTH: 20 bases
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(iv) ANTI-SENSE: no (xi) SEQUENCE DESCRIPTION: SEQ ID NO: 23:

CATCTAAGTA TGCATCTCGG                                               20

(2) INFORMATION FOR SEQ ID NO:24:

(i) SEQUENCE CHARACTERISTICS:
         (A) LENGTH: 20 bases
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(iv) ANTI-SENSE: yes (xi) SEQUENCE DESCRIPTION: SEQ ID NO: 24:

TGCCCCTCGA GCTAAATTAG                                               20
```

METHOD FOR PRODUCING L-LYSINE

BACKGROUND OF THE INVENTION

The present invention relates to a method for producing L-lysine by cultivating a microorganism obtained by modifying a coryneform bacterium used for fermentative production of amino acid or the like by means of a technique based on genetic engineering.

L-Lysine, which is used as a fodder additive, is usually produced by a fermentative method by using an L-lysine-producing mutant strain belonging to the coryneform bacteria. Various L-lysine-producing bacteria known at present are those created by artificial mutation starting from wild type strains belonging to the coryneform bacteria.

As for the coryneform bacteria, there are disclosed a vector plasmid which is autonomously replicable in bacterial cells and has a drug resistance marker gene (see U.S. Pat. No. 4,514,502), and a method for introducing a gene into bacterial cells (for example, Japanese Patent Application Laid-open No. 2-207791). There is also disclosed a possibility for breeding an L-threonine- or L-isoleucine-producing bacterium by using the techniques as described above (see U.S. Pat. Nos. 4,452,890 and 4,442,208). As for breeding of an L-lysine-producing bacterium, a technique is known, in which a gene participating in L-lysine biosynthesis is incorporated into a vector plasmid to amplify the gene in bacterial cells (for example, Japanese Patent Application Laid-open No. 56-160997).

Known genes for L-lysine biosynthesis include, for example, a dihydrodipicolinate reductase gene (Japanese Patent Application Laid-open No. 7-75578) and a diaminopimelate dehydrogenase gene (Ishino, S. et al., *Nucleic Acids Res.*, 15, 3917 (1987)) in which a gene participating in L-lysine biosynthesis is cloned, as well as a phosphoenolpyruvate carboxylase gene (Japanese Patent Application Laid-open No. 60-87788), a dihydrodipicolinate synthase gene (Japanese Patent Publication No. 6-55149), and a diaminopimelate decarboxylase gene (Japanese Patent Application Laid-open No. 60-62994) in which amplification of a gene affects L-lysine productivity.

As for enzymes participating in L-lysine biosynthesis, a case is known for an enzyme which undergoes feedback inhibition when used as a wild type. In this case, L-lysine productivity is improved by introducing an enzyme gene having such mutation that the feedback inhibition is desensitized. Those known as such a gene specifically include, for example, an aspartokinase gene (International Publication Pamphlet of WO 94/25605).

As described above, certain successful results have been obtained by means of amplification of genes for the L-lysine biosynthesis system, or introduction of mutant genes. For example, a coryneform bacterium, which harbors a mutant aspartokinase gene with desensitized concerted inhibition by lysine and threonine, produces a considerable amount of L-lysine (about 25 g/L). However, this bacterium suffers decrease in growth speed as compared with a bacterium harboring no mutant aspartokinase gene. It is also reported that L-lysine productivity is improved by further introducing a dihydrodipicolinate synthase gene in addition to a mutant aspartokinase gene (*Applied and Environmental Microbiology*, 57(6), 1746–1752 (1991)). However, such a bacterium suffers further decrease in growth speed.

No case has been reported in which growth is intended to be improved by enhancing a gene for L-lysine biosynthesis as well. In the present circumstances, no case is known for the coryneform bacteria, in which anyone has succeeded in remarkable improvement in L-lysine yield without restraining growth, by combining a plurality of genes for L-lysine biosynthesis.

SUMMARY OF THE INVENTION

An object of the present invention is to improve the L-lysine yield without restraining the growth of a coryneform bacterium, by enhancing a plurality of genes for L-lysine biosynthesis in combination in the coryneform bacteria.

When an objective substance is produced fermentatively by using a microorganism, the production speed, as well as the yield of the objective substance relative to an introduced material, is an extremely important factor. An objective substance may be produced remarkably inexpensively by increasing the production speed per a unit of fermentation equipment. Accordingly, it is industrially extremely important that the fermentative yield and the production speed are compatible with each other. The present invention proposes a solution for the problem as described above in order to fermentatively produce L-lysine by using a coryneform bacterium.

The principle of the present invention is based on the fact that the growth of a coryneform bacterium can be improved, and the L-lysine-producing speed thereof can be improved by enhancing both of a DNA sequence coding for an aspartokinase in which feedback inhibition by L-lysine and L-threonine is substantially desensitized, and a DNA sequence coding for a diaminopimelate decarboxylase compared with the case in which these DNA sequences are each enhanced singly.

In a first aspect of the present invention, it is provided a recombinant DNA autonomously replicable in cells of coryneform bacteria, comprising a DNA sequence coding for an aspartokinase in which feedback inhibition by L-lysine and L-threonine is substantially desensitized, and a DNA sequence coding for a diaminopimelate decarboxylase. The recombinant DNA further comprising a DNA sequence coding for a phosphoenolpyruvate carboxylase is also provided.

In a second aspect of the present invention, it is provided a coryneform bacterium harboring an aspartokinase in which feedback inhibition by L-lysine and L-threonine is substantially desensitized, and comprising an enhanced DNA sequence coding for a diaminopimelate decarboxylase. The coryneform bacterium further comprising an enhanced DNA sequence coding for a phosphoenolpyruvate carboxylase is also provided.

In a third aspect of the present invention, it is provided a method for producing L-lysine comprising the steps of cultivating any of coryneform bacteria as described in the above in an appropriate medium to allow L-lysine to be produced and accumulated in a culture of the bacterium, and collecting L-lysine from the culture.

Hereinafter, an aspartokinase is referred to as "AK", a gene coding for AK is referred to as "lysC", AK which is desensitized in feedback inhibition by L-lysine and L-threonine is referred to as "mutant AK", and a gene coding for mutant AK is referred to as "mutant lysc", if necessary. Also, a diaminopimelate decarboxylase is referred to as "DDC", a gene coding for DDC is referred to as "lysA", a phosphoenolpyruvate carboxylase is referred to as "PEPC", and a gene coding for PEPC is referred to as "ppc", if necessary.

The coryneform bacteria referred to in the present invention are a group of microorganisms as defined in *Beraey's*

*Manual of Determinative Bacteriology*, 8th ed., p. 599 (1974), which are aerobic Gram-positive non-acid-fast rods having no spore-forming ability. The coryneform bacteria include bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium.

According to the present invention, a production amount and a production speed of L-lysine of coryneform bacteria can be improved.

DETAILED DESCRIPTION OF THE INVENTION

Figure 1:
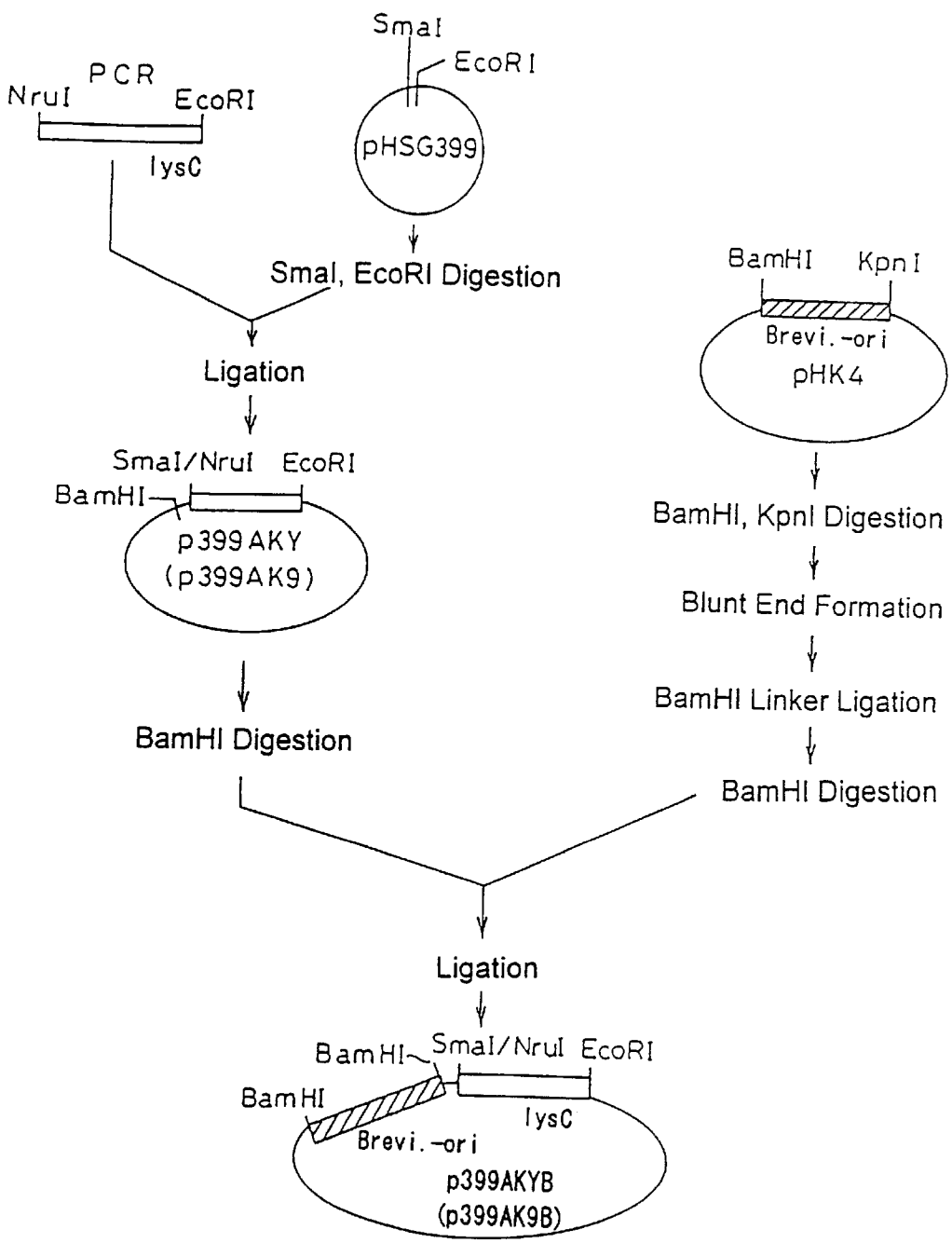
FIG. 1 illustrates a process of construction of plasmids p399AK9B and p399AKYB comprising mutant lysC.

<1> Preparation of genes for L-lysine biosynthesis used for the present invention The genes for L-lysine biosynthesis used in the present invention are obtained respectively by preparing chromosomal DNA from a bacterium as a DNA donor, constructing a chromosomal DNA library by using a plasmid vector or the like, selecting a strain harboring a desired gene, and recovering, from the selected strain, recombinant DNA into which the gene has been inserted. The DNA donor for the gene for L-lysine biosynthesis used in the present invention is not specifically limited provided that the desired gene for L-lysine biosynthesis expresses an enzyme protein which functions in cells of coryneform bacteria. However, the DNA donor is preferably a coryneform bacterium.

All of the genes of lysC, dapA, and ppc originating from coryneform bacteria have known sequences. Accordingly, they can be obtained by performing amplification in accordance with the polymerase chain reaction method (PCR; see White, T. J. et al., *Trends Genet.*, 5, 185 (1989)).

Each of the genes for L-lysine biosynthesis used in the present invention is obtainable in accordance with certain methods as exemplified below.

(1) Preparation of Mutant lysC

A DNA fragment containing mutant lysC can be prepared from a mutant strain in which synergistic feedback inhibition on the AK activity by L-lysine and L-threonine is substantially desensitized (International Publication Pamphlet of WO 94/25605). Such a mutant strain can be obtained, for example, from a group of cells originating from a wild type strain of a coryneform bacterium subjected to a mutation treatment by applying an ordinary mutation treatment such as ultraviolet irradiation and treatment with a mutating agent such as N-methyl-N'-nitro-N-nitrosoguanidine (NTG). The AK activity can be measured by using a method described by Miyajima, R. et al. in *The Journal of Biochemistry* (1968), 63(2), 139–148. The most preferred as such a mutant strain is represented by an L-lysine-producing bacterium AJ3445 (FERM P-1944) derived by a mutation treatment from a wild type strain of *Brevibacterium lactofermentum* ATCC 13869 (having its changed present name of *Corynebacterium glutamicum*).

Alternatively, mutant lysC is also obtainable by an in vitro mutation treatment of plasmid DNA containing wild type lysC. In another aspect, information is specifically known on mutation to desensitize synergistic feedback inhibition on AK by L-lysine and L-threonine (International Publication Pamphlet of WO 94/25605). Accordingly, mutant lysC can be also prepared from wild type lysC on the basis of the information in accordance with, for example, the site-directed mutagenesis method.

A fragment comprising lysC can be isolated from a coryneform bacterium by preparing chromosomal DNA in accordance with, for example, a method of Saito and Miura (H. Saito and K. Miura, *Biochem. Bioohys. Acta*, 72, 619 (1963)), and amplifying lysC in accordance with the polymerase chain reaction method (PCR; see White, T. J. et al., *Trends Genet.*, 5, 185 (1989)).

DNA primers are exemplified by single strand DNA's of 23-mer and 21-mer having nucleotide sequences shown in SEQ ID NOs: 1 and 2 in Sequence Listing in order to amplify, for example, a region of about 1,643 bp coding for lysC based on a sequence known for *Corynebacterium alutamicum* (see *Molecular Microbiology* (1991), 5(5), 1197–1204; *Mol. Gen. Genet.* (1990), 224, 317–324). DNA can be synthesized in accordance with an ordinary method by using DNA synthesizer model 380B produced by Applied Biosystems and using the phosphoamidite method (see *Tetrahedron Letters* (1981), 22, 1859). PCR can be performed by using DNA Thermal Cycler Model PJ2000 produced by Takara Shuzo, and using Taq DNA polymerase in accordance with a method designated by the supplier.

It is preferred that lysC amplified by PCR is ligated with vector DNA autonomously replicable in cells of *E. coli* and/or coryneform bacteria to prepare recombinant DNA, and the recombinant DNA is introduced into cells of *E. coli* beforehand. Such provision makes following operations easy. The vector autonomously replicable in cells of *E. coli* is preferably a plasmid vector which is preferably autonomously replicable in cells of a host, including, for example, pUC19, pUC18, pBR322, pHSG299, pHSG399, pHSG398, and RSF1010.

When a DNA fragment having an ability to allow a plasmid to be autonomously replicable in coryneform bacteria is inserted into these vectors, they can be used as a so-called shuttle vector autonomously replicable in both *E. coli* and coryneform bacteria.

Such a shuttle vector includes the followings. Microorganisms harboring each of vectors and accession numbers in international deposition authorities (in parentheses) are shown.

pHC4: *Escherichia coli* AJ12617 (FERM BP-3532)
pAJ655: *Escherichia coli* AJ11882 (FERM BP-136)
  *Corynebacterium glutamicum* SR8201 (ATCC 39135)
pAJ1844: *Escherichia coli* AJ11883 (FERM BP-137)
  *Corynebacterium glutamicum* SR8202 (ATCC 39136)
pAJ611: *Escherichia coli* AJ11884 (FERM BP-138)
pAJ3148: *Corynebacterium glutamicum* SR8203 (ATCC 39137)
pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant. To the supernatant, polyethylene glycol is added, followed by fractionation and purification by means of cesium chloride-ethidium bromide equilibrium density gradient centrifugation.

*E. coli* can be transformed by introducing a plasmid in accordance with, for example, a method of D. M. Morrison (*Methods in Enzymoloay*, 68, 326 (1979)) or a method in which recipient cells are treated with calcium chloride to increase permeability for DNA (Mandel, M. and Higa, A., *J. Mol. Biol.*, 53, 159 (1970)).

Wild type lysC is obtained when lysC is isolated from an AK wild type strain, while mutant lysC is obtained when lysC is isolated from an AK mutant strain in accordance with the method as described above.

An example of a nucleotide sequence of a DNA fragment containing wild type lysC is shown in SEQ ID NO: 3 in Sequence Listing. An amino acid sequence of α-subunit of a wild type AK protein is deduced from the nucleotide sequence, and is shown in SEQ ID NO: 4 in Sequence Listing together with the DNA sequence. Only the amino acid sequence is shown in SEQ ID NO: 5. An amino acid sequence of β-subunit of the wild type AK protein is deduced from the nucleotide sequence of DNA, and is shown in SEQ ID NO: 6 in Sequence Listing together with the DNA sequence. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

The mutant lysc used in the present invention is not specifically limited provided that it codes for AK in which synergistic feedback inhibition by L-lysine and L-threonine is desensitized. However, the mutant lysC is exemplified by one including mutation in which an amino acid residue corresponding to a 279th alanine residue as counted from the N-terminal is changed into an amino acid residue other than alanine and other than acidic amino acid in the α-subunit, and an amino acid residue corresponding to a 30th alanine residue from the N-terminal is changed into an amino acid residue other than alanine and other than acidic amino acid in the β-subunit in the amino acid sequence of the wild type AK. The amino acid sequence of the wild type AK specifically includes the amino acid sequence shown in SEQ ID NO: 5 in Sequence Listing as the α-subunit, and the amino acid sequence shown in SEQ ID NO: 7 in Sequence Listing as the β-subunit.

Those preferred as the amino acid residue other than alanine and other than acidic amino acid include threonine, arginine, cysteine, phenylalanine, proline, serine, tyrosine, and valine residues.

The codon corresponding to an amino acid residue to be substituted is not specifically limited for its type provided that it codes for the amino acid residue. It is predicted that the amino acid sequence of wild type AK may slightly differ depending on the difference in bacterial species and bacterial strains. AK's, which have mutation based on, for example, substitution, deletion, or insertion of one or more amino acid residues at one or more positions irrelevant to the enzyme activity as described above, can be also used for the present invention. A DNA coding for AK having the spontaneous mutation can be obtained by isolating a DNA which is hybridizable with, for example, the DNA having a part of the nucleotide sequence shown in SEQ ID NO: 3 under the stringent condition. By the "stringent condition" referred to herein is meant a condition under which a specific hybrid is formed, and nonspecific hybrid is not formed. It is difficult to clearly express the condition with numerical values. However, the condition is exemplified by a condition under which, nucleic acid having high homology, for example, DNA's having homology of not less than 90% are hybridized with each other, and nucleic acids having homology lower than the above are not hybridized with each other, or a condition of a temperature of from a melting out temperature (Tm) of a completely-matched hybrid to (Tm−30)° C., preferably from Tm to (Tm−20)° C. and a salt concentration corresponding to 1×SSC, preferably 0.1×ssc.

Other AK's, which have artificial mutation based on, for example, substitution, deletion, or insertion of other one or more amino acid residues, can be also used provided that no influence is substantially exerted on the AK activity, and on the desensitization of synergistic feedback inhibition by L-lysine and L-threonine. A DNA coding for AK having the artificial mutation can be obtained by modifying the nucleotide sequence to give substitution, deletion or insertion of a specified site by, for example, site-specific mutagenesis. Also, lysC having the mutation can be obtained by known mutagen treatment. The mutagen treatment includes in vitro treatment of a DNA containing lysC with hydroxylamine or the like, and treatment of microorganism harboring a DNA containing lysC with a mutagen such as ultraviolet irradiation or a mutagenic agent used for ordinary artificial mutagenesis such as N-methyl-N'-nitro-N-nitrosoguanidine (NTG) or nitric acid. After the mutagen treatment, a site to which mutation is introduced or in which mutation occurs can be determined by selecting a DNA or a microorganism which codes for or produces AK which has the AK activity and whose amino acid sequence is mutated from the DNA subjected to the mutagen treatment or the microorganism subjected to the mutagen treatment. A site of the introduced mutation is not specifically restricted provided that no influence is substantially exerted on the AK activity and on densitization of feedback inhibition. A number of the introduced mutation varies depending on a site or a kind of the mutated amino acid in a steric structure of a protein, and is not specifically restricted provided that no influence is substantially exerted on the AK activity and on densitization of feedback inhibition. The number is usually 1 to 20, preferably 1 to 10.

An AJ12691 strain obtained by introducing a mutant lysC plasmid p399AK9B into an AJ12036 strain (FERM BP-734) as a wild type strain of *Brevibacterium lactofermentum* has been deposited on Apr. 10, 1992 under an accession number of FERM P-12918 in National Institute of Bioscience and Human Technology of Agency of Industrial Science and Technology of Ministry of International Trade and Industry (1-3, Higashi 1-chome, Tsukuba-shi, Ibaraki-ken, 305 Japan), transferred to international deposition based on the Budapest Treaty on Feb. 10, 1995, and deposited under an accession number of FERM BP-4999.

(2) Preparation of lysA

A DNA fragment containing lysA can be prepared from chromosome of a coryneform bacterium by means of PCR. The DNA donor is not specifically limited, however, it is exemplified by *Brevibacterium lactofermentum* ATCC 13869 strain.

In the coryneform bacteria, lysA forms an operon together with argS (arginyl-tRNA synthase gene), and lysA exists downstream from argS. Expression of lysA is regulated by a promoter existing upstream from argS (see *Journal of Bacteriology*, Nov., 7356–7362 (1993)). DNA sequences of these genes are known for *Corynebacterium alutamicum* (see *Molecular Microbiology*, 4(11), 1819–1830 (1990); *Molecular and General Genetics*, 212, 112–119 (1988)), on the basis of which DNA primers for PCR can be prepared. Such DNA primers are specifically exemplified by DNA's of 23-mers respectively having nucleotide sequences shown in SEQ ID NO: 8 in Sequence Listing (corresponding to nucleotide numbers 11 to 33 in a nucleotide sequence described in *Molecular Microbioloay*, 4(11), 1819–1830 (1990)) and SEQ ID NO: 9 (corresponding to nucleotide numbers 1370 to 1392 in a nucleotide sequence described in *Molecular and General Genetics*, 212, 112–119 (1988)). Synthesis of DNA, PCR, and preparation of a plasmid containing obtained lysA can be performed in the same manner as those for lysC described above.

In Example described later on, a DNA fragment containing a promoter, argS, and lysA was used in order to enhance lysA. However, argS is not essential for the present invention. It is allowable to use a DNA fragment in which lysA is ligated just downstream from a promoter.

A nucleotide sequence of a DNA fragment containing argS and lysA, and an amino acid sequence deduced to be encoded by the nucleotide sequence are exemplified in SEQ ID NO: 10. An example of an amino acid sequence encoded by argS is shown in SEQ ID NO: 11, and an example of an amino acid sequence encoded by lysA is shown in SEQ ID NO: 12. In addition to DNA fragments coding for these amino acid sequences, the present invention can equivalently use DNA fragments coding for amino acid sequences substantially the same as the amino acid sequence shown in SEQ ID NO: 12, namely amino acid sequences having mutation based on, for example, substitution, deletion, or insertion of one or more amino acids provided that there is no substantial influence on the DDC activity. The lysA having spontaneous or artificial mutation can be obtained in the same manner as those for the DNA coding for AK having mutation which exerts no influence on the AK activity and on the desensitization of synergistic feedback inhibition by L-lysine and L-threonine.

(3) Preparation of ppc

A DNA fragment containing ppc can be prepared from chromosome of a coryneform bacterium by means of PCR. The DNA donor is not specifically limited, however, it is exemplified by *Brevibacterium lactofermentum* ATCC 13869 strain.

A DNA sequences of the ppc gene is known for *Corynebacterium glutamicum* (see O'Regan, M. et al., Gene, 77, 237–251 (1989)), on the basis of which DNA primers for PCR can be prepared. Such DNA primers are specifically exemplified by DNA's of 23-mers respectively having nucleotide sequences shown in SEQ ID NOs: 13 and 14 in Sequence Listing. Synthesis of DNA, PCR, and preparation of a plasmid containing obtained ppc can be performed in the same manner as those for lysc described above.

A nucleotide sequence of a DNA fragment containing ppc, and an amino acid sequence deduced to be encoded by the nucleotide sequence are shown in SEQ ID NO: 15. Only the amino acid sequence is shown in SEQ ID NO: 16.

In addition to DNA fragments coding for these amino acid sequences, the present invention can equivalently use DNA fragments coding for amino acid sequences substantially the same as the amino acid sequence shown in SEQ ID NO: 16, namely amino acid sequences having mutation based on, for example, substitution, deletion, or insertion of one or more amino acids provided that there is no substantial influence on the PEPC activity. The ppc having spontaneous or artificial mutation can be obtained in the same manner as those for the DNA coding for AK having mutation which exerts no influence on the AK activity and on the desensitization of synergistic feedback inhibition by L-lysine and L-threonine.

The ppc from the coryneform bacteria forms an operon together with gap (glyceraldehyde-3-phosphate dehydrogenase gene), pgk (phosphoglycerate kinase gene) and tpi (triose phosphate isomerase gene), and ppc exists downstream from tpi. Expression of ppc is regulated by a promoter existing upstream from pgk (see Schwinde, J. W. et al., *J. Bacteriol.*, 175(12), 3905–3908 (1993)). Therefore, like the above-mentioned lysA, ppc can be amplified together with pgk and tpi by PCR to use a DNA fragment containing pgk, tpi and ppc. As shown in Example described later on, it is allowable to use a DNA fragment in which a suitable promoter is ligated just upstream from a coding region of PEPC. The promoter includes a promotor of lysC, tac promoter originating from *E. coli*, and trc promoter.

<2> Recombinant DNA and coryneform bacterium of the present invention

The recombinant DNA comprises a DNA sequence coding for an aspartokinase in which feedback inhibition by L-lysine and L-threonine is substantially desensitized, and a DNA sequence coding for a diaminopimelate decarboxylase, and is autonomously replicable in cells of coryneform bacteria. In a preferred embodiment, the recombinant DNA further comprises a DNA sequence coding for a phosphoenolpyruvate carboxylase in addition to the above DNA sequences.

The coryneform bacterium of the present invention harbors an aspartokinase (mutant AK) in which feedback inhibition by L-lysine and L-threonine is substantially desensitized, wherein DNA (lysA) coding for a diaminopimelate decarboxylase is enhanced. In a preferred embodiment, the coryneform bacterium of the present invention is a coryneform bacterium in which DNA (ppc) coding for a phosphoenolpyruvate carboxylase is further enhanced.

The term "enhance" herein refers to the fact that the intracellular activity of an enzyme encoded by the DNA is raised by, for example, increasing the copy number of a gene, using a strong promoter, using a gene coding for an enzyme having a high specific activity, or combining these means.

The coryneform bacterium harboring the mutant AK may be those which produce the mutant aspartokinase as a result of mutation, or those which are transformed by introducing mutant lysC.

Examples of the coryneform bacterium used to introduce the DNA described above include, for example, the following lysine-producing wild type strains:

*Corynebacterium acetoacidophilum* ATCC 13870;
*Corynebacterium acetoglutamicum* ATCC 15806;
*Corynebacterium callunae* ATCC 15991;
*Corynebacterium glutamicum* ATCC 13032;
(*Brevibacterium divaricatum*) ATCC 14020;
(*Brevibacterium lactofermentum*) ATCC 13869;
(*Corynebacterium lilium*) ATCC 15990;
(*Brevibacterium flavum*) ATCC 14067;
*Corynebacterium melassecola* ATCC 17965;
*Brevibacterium saccharolyticum* ATCC 14066;
*Brevibacterium immariophilum* ATCC 14068;
*Brevibacterium roseum* ATCC 13825;
*Brevibacterium thioaenitalis* ATCC 19240;
*Microbacterium ammoniaphilum* ATCC 15354;
*Corynebacterium thermoaminoaenes* AJ12340 (FERM BP-1539).

Other than the bacterial strains described above, those usable as a host include, for example, mutant strains having an L-lysine-producing ability derived from the aforementioned strains. Such artificial mutant strains includes the followings: S-(2-aminoethyl)-cysteine (hereinafter abbreviated as "AEC") resistant mutant strains (for example, *Brevibacterium lactofermentum* AJ11082 (NRRL B-1147), Japanese Patent Publication Nos. 56-1914, 56-1915, 57-14157, 57-14158, 57-30474, 58-10075, 59-4993, 61-35840, 62-24074, 62-36673, 5-11958, 7-112437, and 7-112438); mutant strains which require amino acid such as L-homoserine for their growth (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3,708,395 and 3,825,472); L-lysine-producing mutant strains which exhibit resistance to DL-α-amino-ε-caprolactam, α-aminolauryllactam, aspartate-analog, sulfa drug, quinoid, and N-lauroylleucine; L-lysine-producing mutant strains which exhibit resistance to inhibitors of oxyaloacetate decarboxylase or respiratory system enzymes (Japanese Patent Application Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Application Laid-open Nos. 55-9784 and 56-8692); L-lysine-producing mutant strains which exhibit sensitivity to fluoropyruvic acid or temperature not less than 34° C. (Japanese Patent Application Laid-open Nos. 55-9783 and 53-86090); and producing mutant strains belonging to the genus Brevibacterium or Corynebacterium which exhibit resistance to ethylene glycol and produce L-lysine (U.S. Pat. No. 4,411,997).

In a specified embodiment, in order to enhance the genes for L-lysine biosynthesis in the host as described above, the genes are introduced into the host by using a plasmid vector, transposon or phage vector or the like. Upon the introduction, it is expected to make enhancement to some extent even by using a low copy type vector. However, it is preferred to use a multiple copy type vector. Such a vector includes, for example, plasmid vectors, pAJ655, pAJ1844, pAJ611, pAJ3148, and pAJ440 described above. Besides, transposons derived from coryneform bacteria are described in International Publication Pamphlets of WO02/02627 and WO93/18151, European Patent Publication No. 445385, Japanese Patent Application Laid-open No. 6-46867, Vertes, A. A. et al., Mol. Microbiol., 11, 739–746 (1994), Bonamy, C., et al., Mol. Microbiol., 14, 571–581 (1994), Vertes, A. A. et al., Mol. Gen. Genet., 245, 397–405 (1994), Jagar, W. et al., FEMS Microbiology Letters, 126, 1–6 (1995), Japanese Patent Application Laid-open No. 7-107976, Japanese Patent Application Laid-open No. 7-327680 and the like.

In the present invention, it is not indispensable that the mutant lysC is necessarily enhanced. It is allowable to use those which have mutation on lysC on chromosomal DNA, or in which the mutant lysC is incorporated into chromosomal DNA. Alternatively, the mutant lysC may be introduced by using a plasmid vector. On the other hand, lysA and ppc are preferably enhanced in order to efficiently produce L-lysine.

Each of the genes of lysC, lysA, and ppc may be successively introduced into the host by using different vectors respectively. Alternatively, two or three species of the genes may be introduced together by using a single vector. When different vectors are used, the genes may be introduced in any order, however, it is preferred to use vectors which have a stable sharing and harboring mechanism in the host, and which are capable of co-existing with each other.

A coryneform bacterium harboring the mutant AK and further comprising enhanced lysA is obtained, for example, by introducing, into a host coryneform bacterium, a recombinant DNA containing mutant lysC, lysA and ppc autonomously replicable in cells of coryneform bacteria.

A coryneform bacterium further comprising enhanced ppc in addition to mutant lysC and lysA is obtained, for example, by introducing, into a host coryneform bacterium, a recombinant DNA containing mutant lysC, lysA, and ppc autonomously replicable in cells of coryneform bacteria. Also, a coryneform bacterium comprising enhanced mutant lysC, lysA and ppc is obtained by introducing, into a coryneform bacterium comprising enhanced mutant lysC and lysA, a recombinant DNA containing ppc autonomously replicable in cells of coryneform bacteria.

The above-mentioned recombinant DNAs can be obtained, for example, by inserting each of the genes participating in L-lysine biosynthesis into a vector such as plasmid vector, transposon or phage vector as described above.

In the case in which a plasmid is used as a vector, the recombinant DNA can be introduced into the host in accordance with an electric pulse method (Sugimoto et al., Japanese Patent Application Laid-open No. 2-207791). Amplification of a gene using transposon can be performed by introducing a plasmid which carrying a transposon into the host cell and inducing transposition of the transposon.

<3> Method for producing L-lysine

L-Lysine can be efficiently produced by cultivating, in an appropriate medium, the coryneform bacterium comprising the enhanced genes for L-lysine biosynthesis as described above, to allow L-lysine to be produced and accumulated in a culture of the bacterium, and collecting L-lysine from the culture.

The medium to be used is exemplified by an ordinary medium containing a carbon source, a nitrogen source, inorganic ions, and optionally other organic components.

As the carbon source, it is possible to use sugars such as glucose, fructose, sucrose, molasses, and starch hydrolysate; and organic acids such as fumaric acid, citric acid, and succinic acid.

As the nitrogen source, it is possible to use inorganic ammonium salts such as ammonium sulfate, ammonium chloride, and ammonium phosphate; organic nitrogen such as soybean hydrolysate; ammonia gas; and aqueous ammonia.

As organic trace nutrient sources, it is desirable to contain required substances such as vitamin $B_1$ and L-homoserine or yeast extract or the like in appropriate amounts. Other than the above, potassium phosphate, magnesium sulfate, iron ion, manganese ion and so on are added in small amounts, if necessary.

Cultivation is preferably carried out under an aerobic condition for about 30 to 90 hours. The cultivation temperature is preferably controlled at 25° C. to 37° C., and pH is preferably controlled at 5 to 8 during cultivation. Inorganic or organic, acidic or alkaline substances, or ammonia gas or the like can be used for pH adjustment. L-lysine can be collected from a culture by combining an ordinary ion exchange resin method, a precipitation method, and other known methods.

EXAMPLES

The present invention will be more specifically explained below with reference to Examples.

Example 1

Preparation of Wild Type lysC Gene and Mutant lysC Gene from *Brevibacterium lactofermentum*

<1> Preparation of Wild Type and Mutant lysC's and Preparation of Plasmids Containing Them A strain of *Brevibacterium lactofermentum* ATCC 13869, and an L-lysine-producing mutant strain AJ3445 (FERM P-1944) obtained from the ATCC 13869 strain by a mutation treatment were used as chromosomal DNA donors. The AJ3445 strain had been subjected to mutation so that lysC was changed to involve substantial desensitization from concerted inhibition by lysine and threonine (*Journal of Biochemistry*, 68, 701–710 (1970)).

A DNA fragment containing lysC was amplified from chromosomal DNA in accordance with the PCR method polymerase chain reaction; see White, T. J. et al., *Trends Genet.*, 5, 185 (1989)). As for DNA primers used for amplification, single strand DNA's of 23-mer and 21-mer having nucleotide sequences shown in SEQ ID NOs: 1 and 2 were synthesized in order to amplify a region of about 1,643 bp coding for lysC on the basis of a sequence known for *Corynebacterium glutamicum* (see *Molecular Microbiology* (1991), 5(5), 1197–1204; and *Mol. Gen. Genet.* (1990), 224, 317–324). DNA was synthesized in accordance with an ordinary method by using DNA synthesizer model 380B produced by Applied Biosystems and using the phosphoamidite method (see *Tetrahedron Letters* (1981), 22, 1859).

The-gene was amplified by PCR by using DNA Thermal Cycler Model PJ2000 produced by Takara Shuzo, and using Taq DNA polymerase in accordance with a method designated by the supplier. An amplified gene fragment of 1,643 kb was confirmed by agarose gel electrophoresis. After that, the fragment excised from the gel was purified in accordance with an ordinary method, and it was digested with restriction enzymes NruI (produced by Takara Shuzo) and EcoRI (produced by Takara Shuzo).

pHSG399 (see Takeshita, S. et al., Gene (1987), 61, 63–74) was used as a cloning vector for the gene fragment. pHSG399 was digested with restriction enzymes SmaI (produced by Takara Shuzo) and EcoRI, and it was ligated with the amplified lysC fragment. DNA was ligated by using DNA ligation kit (produced by Takara Shuzo) in accordance with a designated method. Thus plasmids were prepared, in which the lysC fragments amplified from chromosomes of *Brevibacterium lactofermentum* were ligated with pHSG399 respectively. A plasmid comprising lysC from ATCC 13869 (wild type strain) was designated as p399AKY, and a plasmid comprising lysC from AJ3463 (L-lysine-producing bacterium) was designated as p399AK9.

A DNA fragment (hereinafter referred to as "Brevi.-ori") having an ability to make a plasmid autonomously replicable in bacteria belonging to the genus Corynebacterium was introduced into p399AKY and p399AK9 respectively to prepare plasmids carrying lysC autonomously replicable in bacteria belonging to the genus Corynebacterium. Brevi.-ori was prepared from a plasmid vector pHK4 containing Brevi.-ori and autonomously replicable in cells of both *Escherichia coli* and bacteria belonging to the genus Corynebacterium. pHK4 was constructed by digesting pHC4 with KpnI (produced by Takara Shuzo) and BamHI (produced by Takara Shuzo), extracting a Brevi.-ori fragment, and ligating it with pHSG298 having been also digested with KpnI and BamHI (see Japanese Patent Application Laid-open No. 5-7491). pHK4 gives kanamycin resistance to a host. *Escherichia coli* harboring pHK4 was designated as *Escherichia coli* AJ13136, and deposited on Aug. 1, 1995 under an accession number of FERM BP-5186 in National Institute of Bioscience and Human Technology of Agency of Industrial Science and Technology of Ministry of International Trade and Industry (1-3, Higashi 1-chome, Tsukuba-shi, Ibaraki-ken, 305 Japan).

pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKY and p399AK9 having been also digested with BamHI respectively to prepare plasmids each containing the lysC gene autonomously replicable in bacteria belonging to the genus Corynebacterium.

A plasmid containing the wild type lysC gene originating from p399AKY was designated as p399AKYB, and a plasmid containing the mutant lysC gene originating from p399AK9 was designated as p399AK9B. The process of construction of p399AK9B and p399AKYB is shown in FIG. 1. A strain AJ12691 obtained by introducing the mutant lysC plasmid p399AK9B into a wild type strain of *Brevibacterium lactofermentum* (AJ12036 strain, FERM BP-734) was deposited on Apr. 10, 1992 under an accession number of FERM P-12918 in National Institute of Bioscience and Human Technology of Agency of Industrial Science and Technology of Ministry of International Trade and Industry (1-3, Higashi 1-chome, Tsukuba-shi, Ibaraki-ken, 305 Japan), transferred to international deposition based on the Budapest Treaty on Feb. 10, 1995, and deposited under an accession number of FERM BP-4999.

<2> Determination of Nucleotide Sequences of Wild Type lysC and Mutant lysC from *Brevibacterium lactofermentum*

The plasmid p399AKY containing the wild type lysC and the plasmid p399AK9 containing the mutant lysC were prepared from the respective transformants to determine nucleotide sequences of the wild type and mutant lysC's. Nucleotide sequence determination was performed in accordance with a method of Sanger et al. (for example, F. Sanger et al., *Proc. Natl. Acad. Sci.*, 74, 5463 (1977)).

The nucleotide sequence of wild type lysC encoded by p399AKY is shown in SEQ ID NO: 3 in Sequence Listing. On the other hand, the nucleotide sequence of mutant lysC encoded by p399AK9 had only mutation of one nucleotide such that 1051st G was changed into A in SEQ ID NO: 3 as compared with wild type lysc. It is known that lysC of *Corynebacterium glutamicum* has two subunits (α, β) encoded in an identical reading frame on an identical DNA strand (see Kalinowski, J. et al., *Molecular Microbiology* (1991) 5(5), 1197–1204). Judging from homology, it is assumed that the gene sequenced herein also has two subunits (α, β) encoded in an identical reading frame on an identical DNA strand.

An amino acid sequence of the α-subunit of the wild type AK protein deduced from the nucleotide sequence of DNA is shown in SEQ ID NO: 4 together with the DNA sequence. Only the amino acid sequence is shown in SEQ ID NO: 5. An amino acid sequence of the β-subunit of the wild type AK protein deduced from the nucleotide sequence of DNA is shown in SEQ ID NO: 6 together with DNA sequence. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

On the other hand, mutation on the sequence of mutant lysC means occurrence of amino acid residue substitution such that a 279th alanine residue of the α-subunit is changed into a threonine residue, and a 30th alanine residue of the β-subunit is changed into a threonine residue in the amino acid sequence of the wild type AK protein (SEQ ID NOs: 5, 7).

Example 2

Preparation of lysA from *Brevibacterium lactofermentum*

<1> Preparation of lysA and Construction of Plasmid Containing lysA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing argS, lysA, and a promoter of an operon containing them was amplified from the chromosomal DNA in accordance with PCR. As for DNA primers used for amplification, synthetic DNA's of 23-mers having nucleotide sequences shown in SEQ ID NOs: 8 and 9 in Sequence Listing respectively were used in order to amplify a region of about 3.6 kb coding for arginyl-tRNA synthase and DDC on the basis of a sequence known for *Corynebacterium glutamicum* (see *Molecular Microbioloby*, 4(11), 1819–1830 (1990); *Molecular and General Genetics*, 212, 112–119 (1988)). Synthesis of DNA and PCR were performed in the same manner as described in Example 1. pHSG399 was used as a cloning vector for the amplified gene fragment of 3,579 bp. pHSG399 was digested with a restriction enzyme SmaI (produced by Takara Shuzo), and was ligated with the DNA fragment containing amplified lysA. A plasmid obtained as described above, which had lysA originating from ATCC 13869, was designated as p399LYSA.

Figure 2:
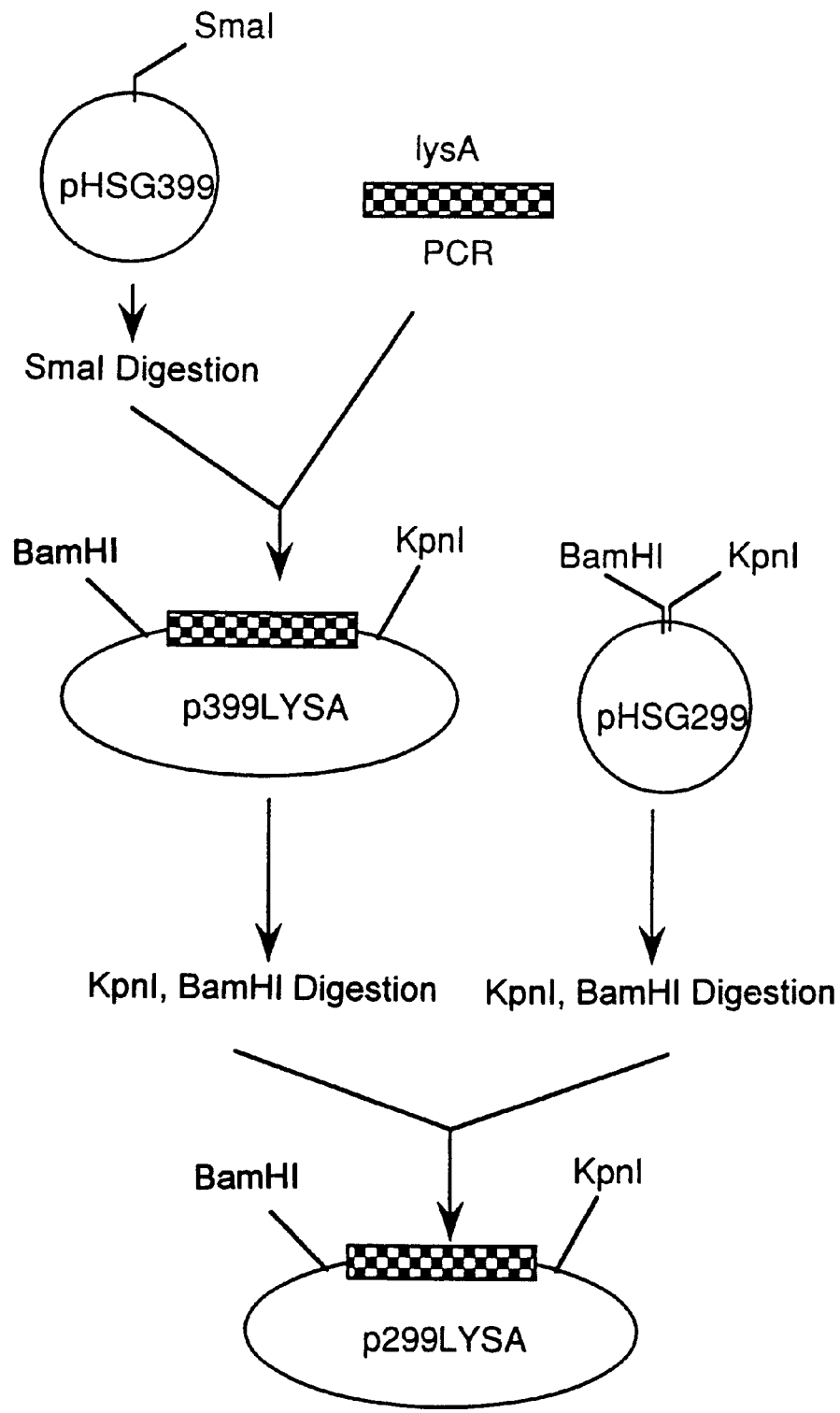
FIG. 2 illustrates a process of construction of a plasmid p299LYSA comprising lysA.

A DNA fragment containing lysA was extracted by digesting p399LYSA with KpnI (produced by Takara Shuzo) and BamHI (produced by Takara Shuzo). This DNA fragment was ligated with pHSG299 having been digested with KpnI and BamHI. An obtained plasmid was designated as p299LYSA. The process of construction of p299LYSA is shown in FIG. 2.

Figure 3:
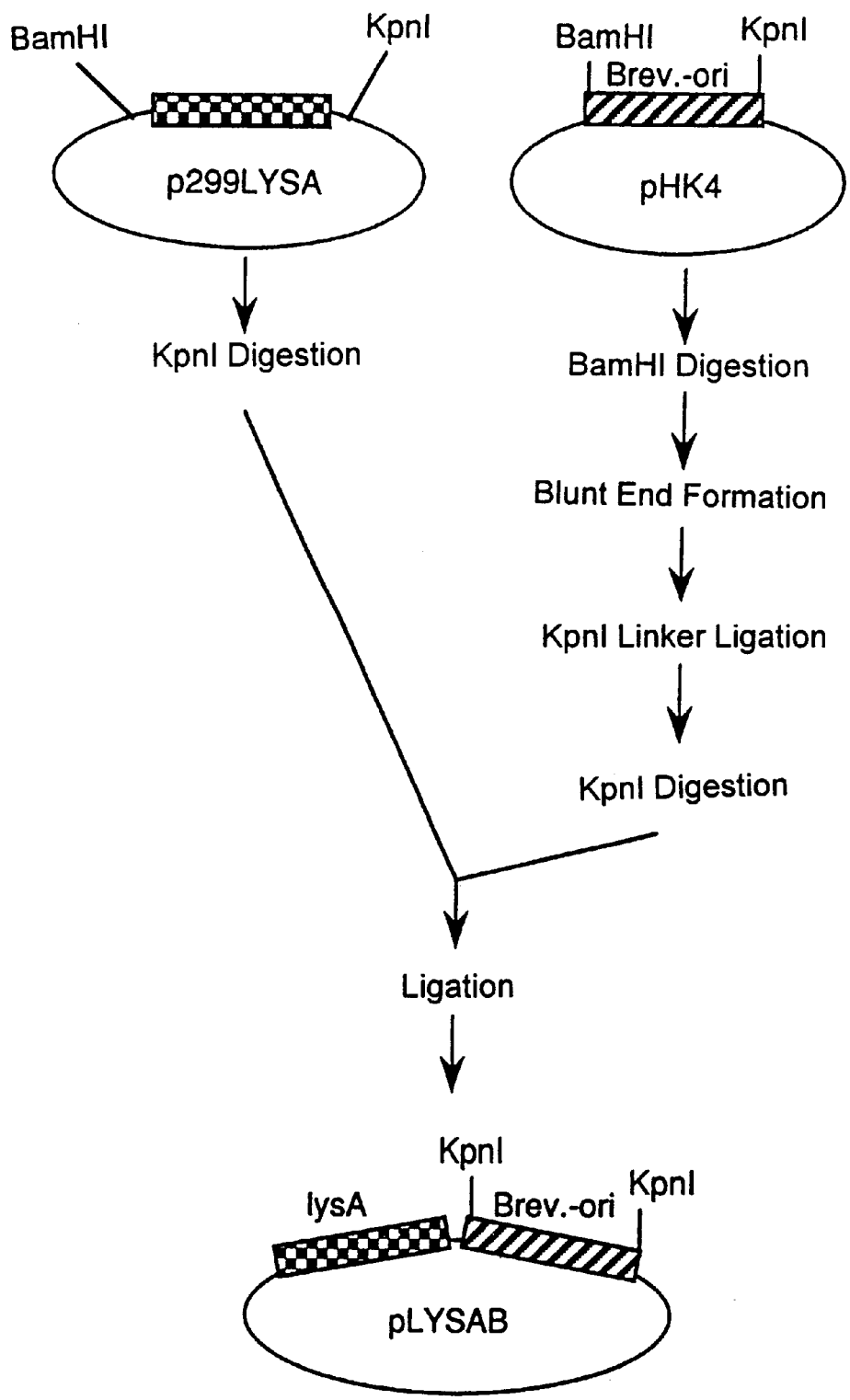
FIG. 3 illustrates a process of construction of a plasmid pLYSAB comprising lysA and Brevi.-ori.

Brevi.-ori was introduced into the obtained p299LYSA to construct a plasmid carrying lysA autonomously replicable in coryneform bacteria. pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p299LYSA having been also digested with KpnI to prepare a plasmid containing lysA autonomously replicable in coryneform bacteria. The prepared plasmid was designated as pLYSAB. The process of construction of pLYSAB is shown in FIG. 3.

<2> Determination of Nucleotide Sequence of lysA from *Brevibacterium lactofermentum*

Plasmid DNA of p299LYSA was prepared, and its nucleotide sequence was determined in the same manner as described in Example 1. A determined nucleotide sequence and an amino acid sequence deduced to be encoded by the nucleotide sequence are shown in SEQ ID NO: 10. Concerning the nucleotide sequence, an amino acid sequence encoded by argS and an amino acid sequence encoded by lysA are shown in SEQ ID NOs: 11 and 12, respectively.

Example 3

Preparation of ppc from *Brevibacterium lactofermentum*

<1> Preparation of ppc

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing ppc was amplified from the chromosomal DNA in accordance with PCR. As for DNA primers used for amplification, synthetic DNA's of 23-mers having nucleotide sequences shown in SEQ ID NOs: 13 and 14 in Sequence Listing respectively were used in order to amplify a region of about 3.3 kb coding for PEPC on the basis of a sequence known for *Corynebacterium glutamicum* (see O'Regan, M. et al., Gene, 77, 237–251 (1989)). Synthesis of DNA and PCR were performed in the same manner as described in Example 1.

An amplified gene fragment of about 3,300 bp was confirmed by agarose gel electrophoresis, and then the fragment extracted from the gel was purified by an ordinary method and digested with a restriction enzyme SalI (produced by Takara Shuzo). pHSG399 was used as a cloning vector for ppc. pHSG399 was digested with a restriction enzyme SalI (produced by Takara Shuzo), and was ligated with the DNA fragment containing amplified ppc. A plasmid obtained as described above, which had ppc originating from ATCC 13869, was designated as pPCF.

<2> Ligation of ppc Gene with lysC Promotor

The pPCF obtained as described in the above was digested with a restriction enzyme DraI (produced by Takara Shuzo). After a DNA fragment of about 150 bp upstream of the PEPC structural gene was removed, self-ligation was effected to obtain a plasmid pPCFds. pPCFds was digested with a restriction enzyme SalI (produced by Takara Shuzo), and cleaved edges were blunt-ended. Blunt end formation was performed by using DNA Blunting kit (produced by Takara Shuzo) in accordance with a designated method.

p399AKYB containing wild type lysC obtained in Example 1 was digested with restriction enzymes ApaLI and PstI (both produced by Takara Shuzo), and cleaved edges were blunt-ended in the same manner as above. A smaller fragment among the obtained two DNA fragments contains Brevi.-ori and a promoter of lysc. This fragment was ligated with the above-mentioned fragment obtained by digesting pPCFds with SalI and blunt-ended by using DNA Ligation kit (produced by Takara Shuzo).

Figure 4:
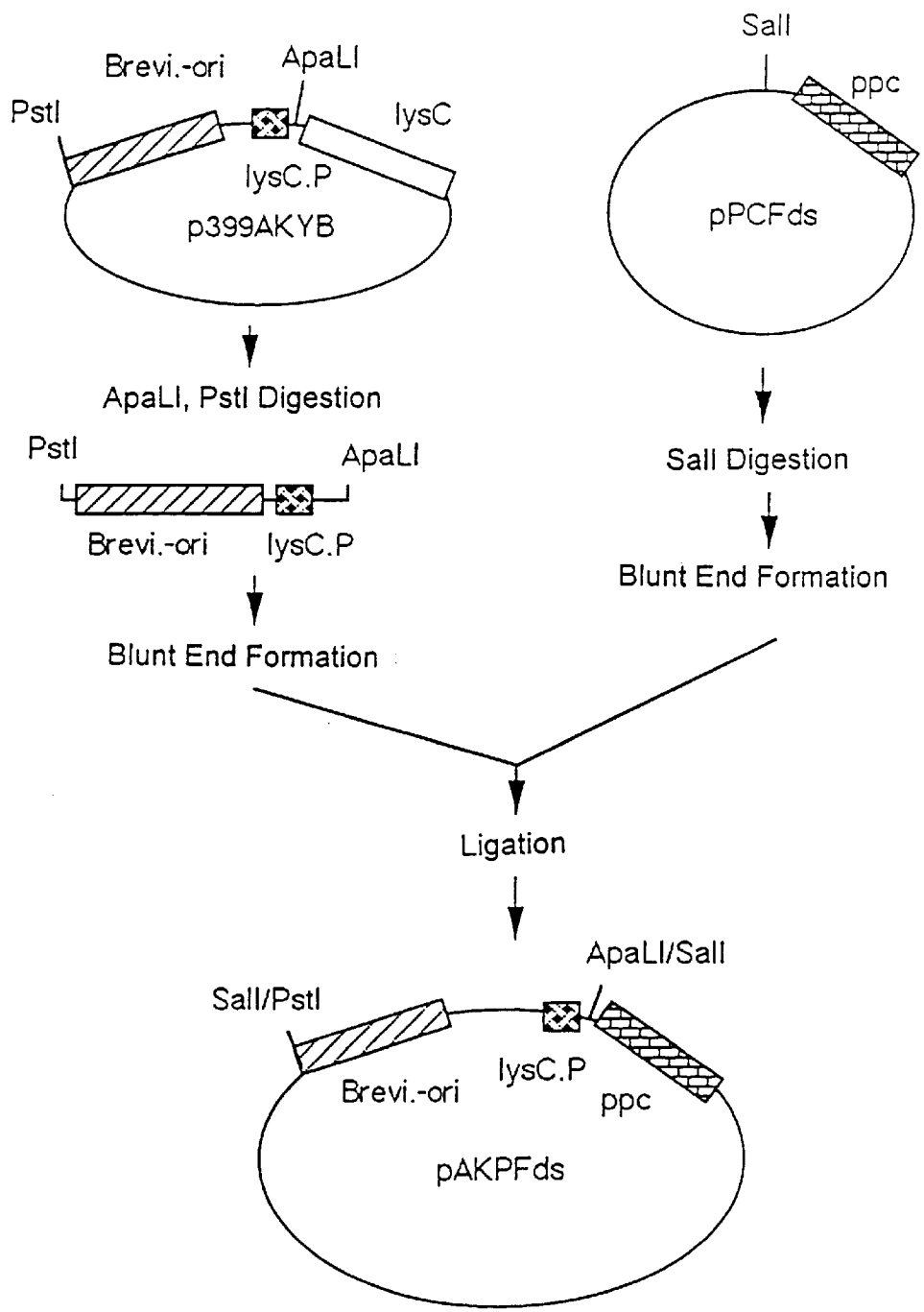
FIG. 4 illustrates a process of construction of a plasmid pAKPFds comprising a PEPC structural gene.

A DNA in a ligation solution was introduced into *Brevibacterium lactofermentum* ATCC 13869 in accordance with an electric pulse method (Sugimoto et al., Japanese Patent Application Laid-open No. 2-207791). Transformants were selected on a complete medium containing 5 μg/ml of chloramphenicol. Plasmid DNA was collected from the transformants, and digested with EcoRI to obtain a plasmid in which the lysC promoter was ligated with the ppc structural gene in normal orientation. The obtained plasmid was designated as pAKPFds. The process of construction of pAKPFds is shown in FIG. 4. The ppc ligated with the lysC promoter is hereinafter referred to as "wild type high expression ppc".

<3> Insertion of Wild Type High Expression ppc Into Vector

The wild type high expression ppc obtained in the above was amplified by PCR to insert it into a vector having a replication origin autonomously replicable in coryneform bacteria other than Brevi.-ori. As for DNA primers, an oligonucleotide corresponding to the lysC promoter portion (SEQ ID NO: 7), which was synthesized on the basis of a sequence of lysC known for *Corynebacterium glutamicum* (see *Molecular Microbioloay*, 5(5), 1197–1204 (1991); *Mol. Gen. Genet.*, 224, 317–324 (1990)), and an oligonucleotide corresponding to the ppc portion (SEQ ID NO: 8), which was synthesized on the basis of a sequence of ppc known for *Corynebacterium glutamicum* (see O'Regan, M. et al., Gene, 77, 237–251 (1989)). These primers were designed so that a fragment of about 3,150 bp containing the wild type high expression ppc could be amplified and a terminal of the amplified DNA fragment could be digested a restriction enzyme KpnI. Synthesis of DNA and PCR were performed in the same manner as described in Example 1.

Figure 5:
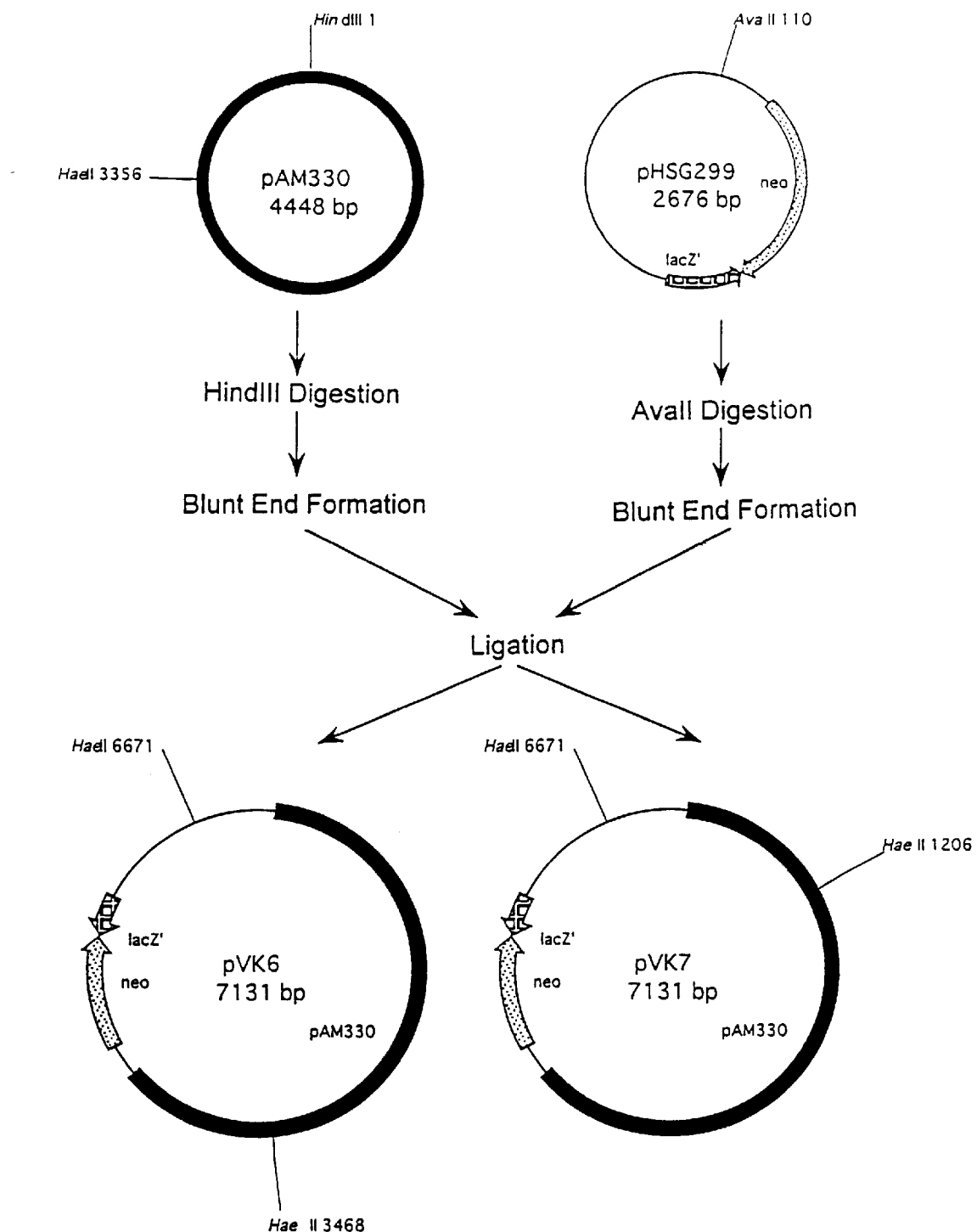
FIG. 5 illustrates a process of construction of novel cloning vectors for Coryneform bacteria, pVK6 and pVK7.

A cloning vector for coryneform bacteria, pVK7, which was newly constructed, was used as a vector for introducing the wild type high expression ppc into coryneform bacteria. pVK7 was constructed by ligating pHSG299, a vector for *E. coli* (Km$^r$; Takeshita, S. et al., Gene, 61, 63–74 (1987)) with pAM330, a cryptic plasmid for *Brevibacterium lactofermentum* as described below. pHSG299 was digested with a restriction enzyme resulting one cleavage site, AvaII (produced by Takara Shuzo), blunt-ended by using T4 DNA polymerase, and ligated with pAM330 having been digested with HindIII (produced by Takara Shuzo) and blunt-ended by using T4 DNA polymerase. Depending on orientation of the inserted pAM330 in pHSG299, the two obtained plasmids were designated as pVK6 and pVK7, and pVK7 was used for the following experiments. pVK7 is autonomously replicable in both of *E. coli* and *Brevibacterium lactofermentum* and has a multiple cloning site originating from pHSG299 and lacZ'. The process of construction of pVK6 and pVK7 is shown in FIG. 5.

Figure 6:
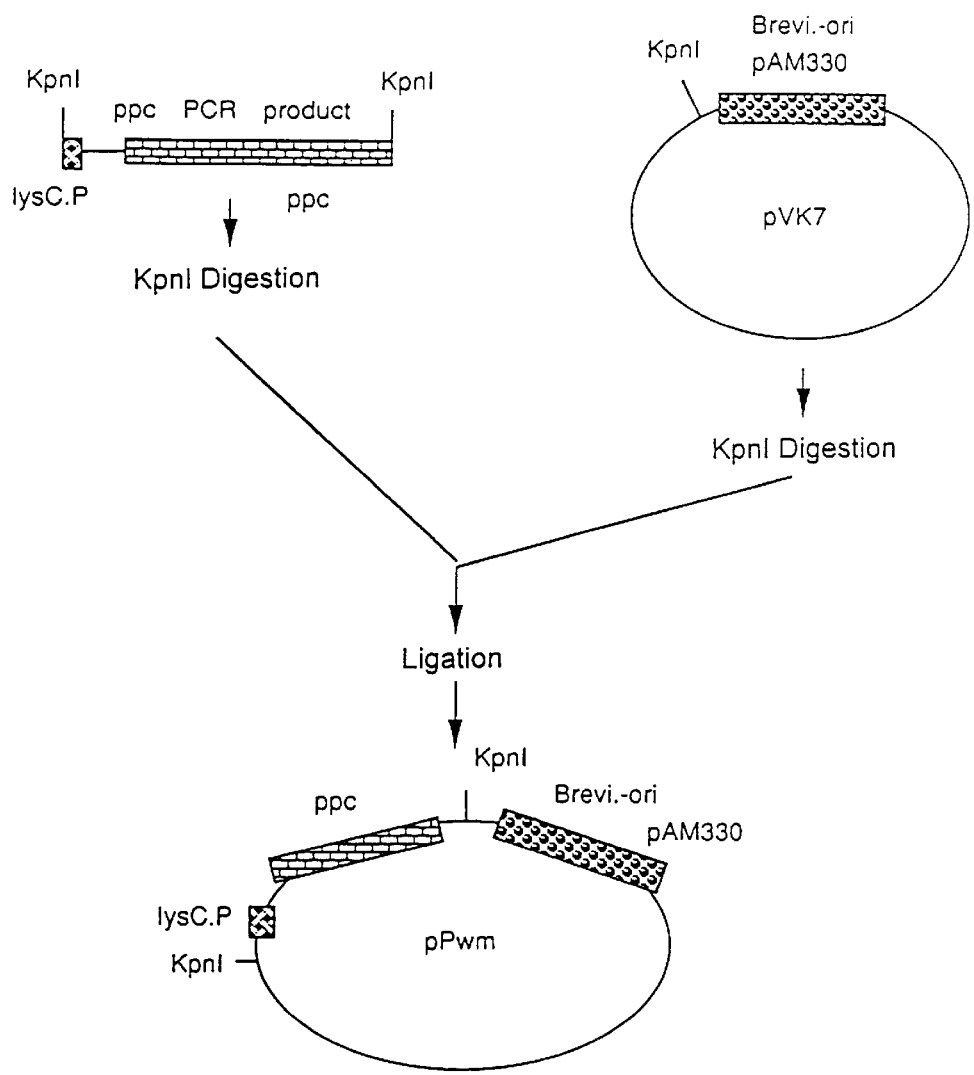
FIG. 6 illustrates a process of construction of a plasmid pPwm comprising a wild type high expression ppc.

An amplified gene fragment of about 3,150 bp was confirmed by agarose gel electrophoresis, and then the fragment extracted from the gel was purified by an ordinary method and digested with a restriction enzyme KpnI (produced by Takara Shuzo). The DNA fragment was ligated with pVK7 having been digested with a restriction enzyme KpnI. The prepared plasmid was designated as pPwm. The process of construction of pPwm is shown in FIG. 6.

Example 4

Preparation of plasmid comprising combination of mutant lysC and lysA

Figure 7:
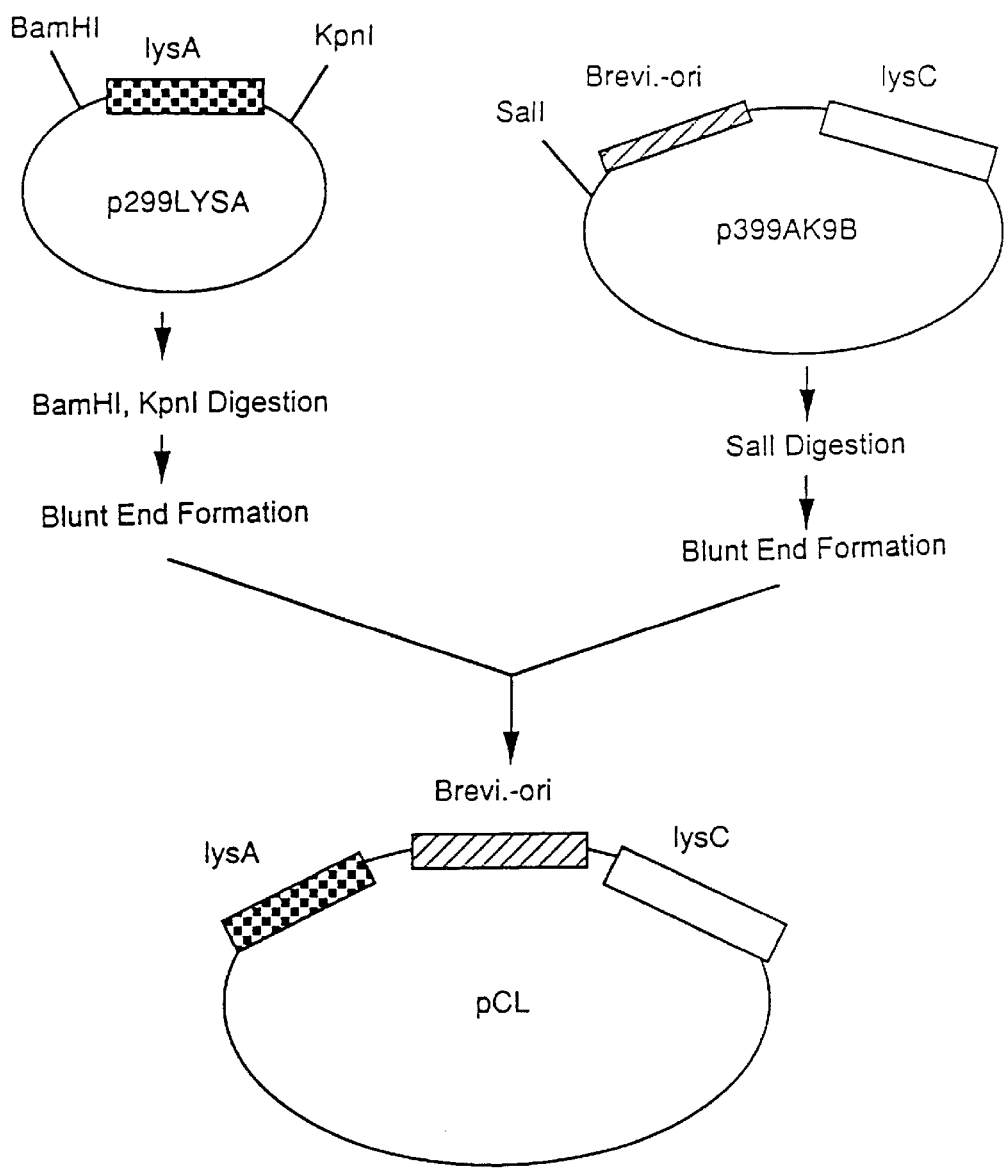
FIG. 7 illustrates a process of construction of a plasmid pCL comprising mutant lysC, lysA and Brevi.-ori.

A plasmid containing mutant lysC, lysA, and a replication origin for coryneform bacteria was prepared from plasmid p399AK9B containing mutant lysC and Brevi.-ori and plasmid p299LYSA containing lysA. p299LYSA was digested with restriction enzymes BamHI and KpnI (both produced by Takara Shuzo) and blunt-ended. Blunt end formation was performed by using DNA Blunting kit (produced by Takara Shuzo) in accordance with a designated method. The obtained DNA fragment was ligated with p399AK9B having been digested with SalI and blunt-ended. Thus, a plasmid containing mutant lysC and lysA autonomously replicable in coryneform bacteria was prepared, and designated as pCL. The process of construction of pCL is shown in FIG. 7.

Comparative Example 1

Preparation of dapA, dapB and ddh from *Brevibacterium lactofermentum*

As genes associated with L-lysine biosynthesis other than lysC, lysA and ppc, dapA (dihydrodipicolinate synthase gene), dapB (dihydrodipicolinate reductase gene) and ddh (diaminopimelate dehydrogenase gene) were obtained as follows.

<1> Preparation of daNA and Construction of Plasmid Containing dapA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapA was amplified from the chromosomal DNA in accordance with PCR. As for DNA primers used for amplification, DNA's of 23-mers having nucleotide sequences shown in SEQ ID NOs: 21 and 22 in Sequence Listing respectively were synthesized in order to amplify a region of about 1.5 kb coding for DDPS on the basis of a sequence known for *Corynebacterium glutamicum* (see *Nucleic Acids Research*, 18(21), 6421 (1990); EMBL accession No. X53993). Synthesis of DNA and PCR were performed in the same manner as described in Example 1. pCR1000 (produced by Invitrogen, see *Bio/Technoloay*, 9, 657–663 (1991)) was used as a cloning vector for the amplified gene fragment of 1,411 bp, and was ligated with the amplified dapA fragment. Ligation of DNA was performed by using DNA ligation kit (produced by Takara Shuzo) in accordance with a designated method. Thus a plasmid was constructed, in which the dapA fragment of 1,411 bp amplified from chromosome of *Brevibacterium lactofermentum* was ligated with pCR1000. The plasmid obtained as described above, which had dapA originating from ATCC 13869, was designated as pCRDAPA.

A transformant strain AJ13106 obtained by introducing PCRDAPA into *E. coli* JM109 strain has been internationally deposited since May 26, 1995 under an accession number of FERM BP-5113 in National Institute of Bioscience and Human Technology of Agency of Industrial Science and Technology of Ministry of International Trade and Industry (1-3, Higashi 1-chome, Tsukuba-shi, Ibaraki-ken, 305 Japan) based on the Budapest Treaty.

Figure 8:
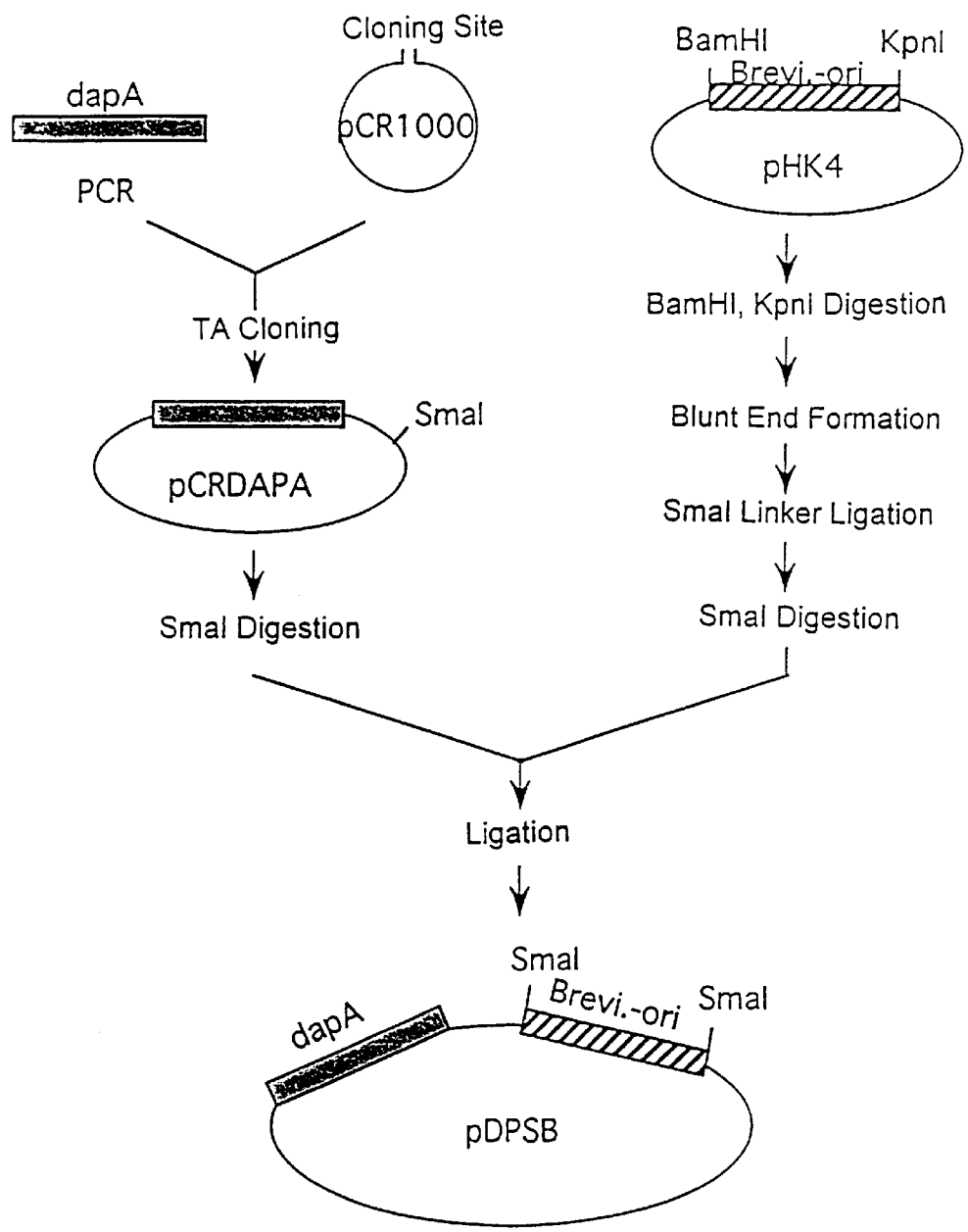
FIG. 8 illustrates a process of construction of a plasmid pDPSB comprising dapA and Brevi.-ori.

Brevi.-ori was introduced into the prepared pCRDAPA to construct a plasmid carrying dapA autonomously replicable in coryneform bacteria. pHK4 was digested with restriction enzymes KpnI and BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated SmaI linker (produced by Takara Shuzo) was ligated to make modification so that the DNA fragment corresponding to the Brevi.-ori portion might be excised from pHK4 by digestion with only SmaI. This plasmid was digested with SmaI, and the generated Brevi.-ori DNA fragment was ligated with pCRDAPA having been also digested with SmaI to prepare a plasmid containing dapA autonomously replicable in coryneform bacteria. This plasmid was designated as pDPSB. The process of construction of pDPSB(Kmr) is shown in FIG. 8.

<2> Preparation of dapB and Construction of Plasmid Containing dapB

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapB was amplified from the chromosomal DNA in accordance with PCR. As for DNA primers used for amplification, DNA's of 23-mers having nucleotide sequences depicted in SEQ ID NOs: 19 and 20 in Sequence Listing respectively were synthesized in order to amplify a region of about 2.0 kb coding for DDPR on the basis of a sequence known for *Brevibacterium lactofermentum* (see *Journal of Bacteriology*, 175(9), 2743–2749 (1993)). Synthesis of DNA and PCR were performed in the same manner as described in Example 1. pCR-Script (produced by Invitrogen) was used as a cloning vector for the amplified gene fragment of 2,001 bp, and was ligated with the amplified dapB fragment. Thus a plasmid was constructed, in which the dapB fragment of 2,001 bp amplified from chromosome of *Brevibacterium lactofermentum* was ligated with pCR-Script. The plasmid obtained as described above, which had dapB originating from ATCC 13869, was designated as pCRDAPB. A transformant strain AJ13107 obtained by introducing pCRDAPB into *E. coli* JM109 strain has been internationally deposited since May 26, 1995 under an accession number of FERM BP-5114 in National Institute of Bioscience and Human Technology of Agency of Industrial Science and Technology of Ministry of International Trade and Industry (1-3, Higashi 1-chome, Tsukuba-shi, Ibaraki-ken, 305 Japan) based on the Budapest Treaty.

A fragment of 1,101 bp containing a structural gene of DDPR was extracted by digesting pCRDAPB with EcoRV and SphI. This fragment was ligated with pHSG399 having been digested with HincII and SphI to prepare a plasmid. The prepared plasmid was designated as p399DPR.

Figure 9:
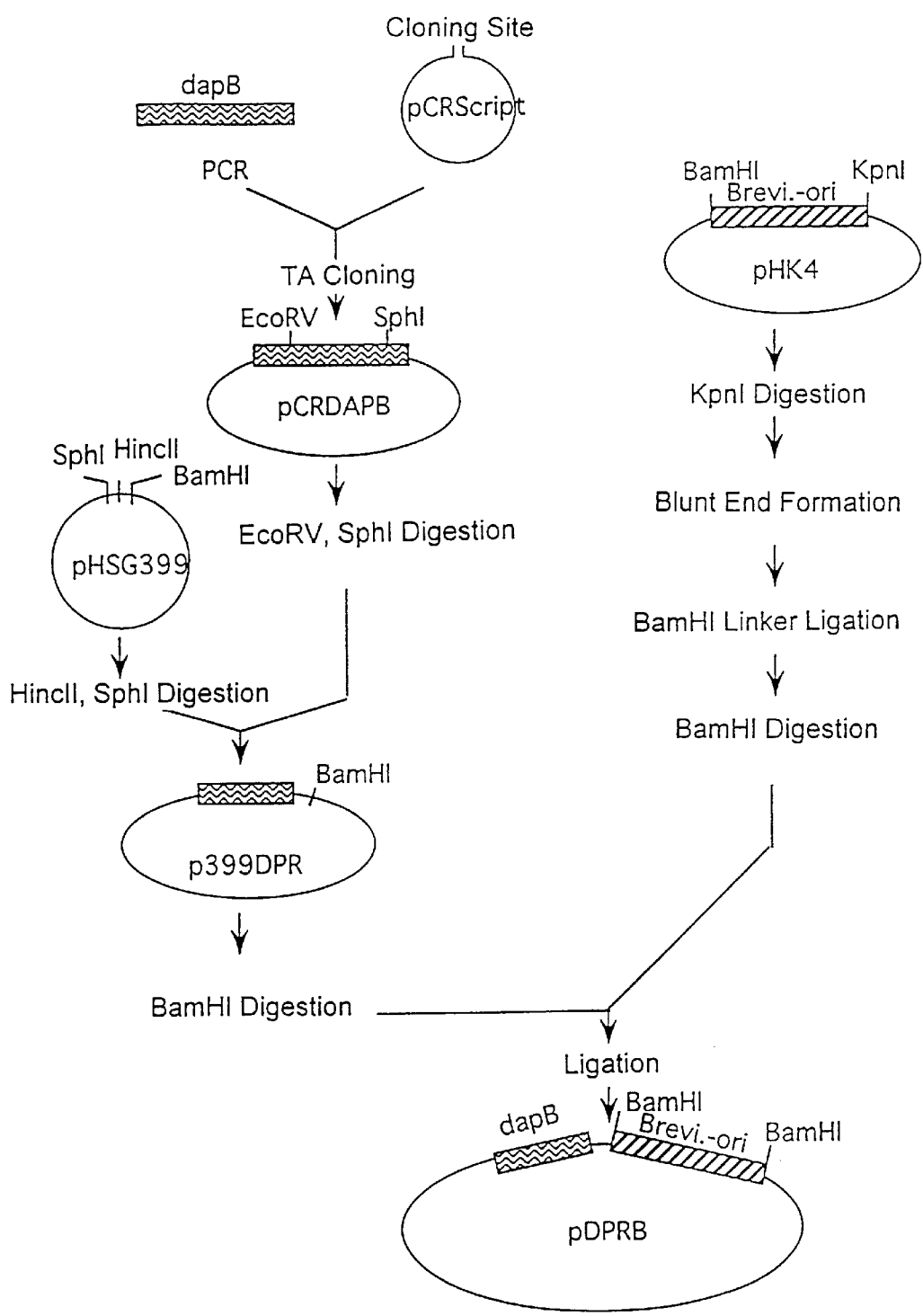
FIG. 9 illustrates a process of construction of a plasmid pDPRB comprising dapB and Brevi.-ori.

Brevi.-ori was introduced into the prepared p399DPR to construct a plasmid carrying dapB autonomously replicable in coryneform bacteria. pHK4 was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399DPR having been also digested with BamHI to prepare a plasmid containing dapB autonomously replicable in coryneform bacteria. The prepared plasmid was designated as pDPRB. The process of construction of PDPRB is shown in FIG. 9.

<3> Preparation of ddh and Construction of Plasmid Containing ddh

A ddh gene was obtained by amplifying the ddh gene from chromosomal DNA of *Brevibacterium lactofermentum* ATCC 13869 in accordance with the PCR method by using two oligonucleotide primers (SEQ ID NOs: 23, 24) prepared on the basis of a known nucleotide sequence of a ddh gene of *Corynebacterium glutamicum* (Ishino, S. et al., *Nucleic Acids Res.*, 15, 3917 (1987)). An obtained amplified DNA fragment was digested with EcoT22I and AvaI, and cleaved edges were blunt-ended. After that, the fragment was inserted into a SmaI site of pMW119 to obtain a plasmid PDDH.

Next, pDDH was digested with SalI and EcoRI, followed by blunt end formation. After that, an obtained fragment was ligated with pUC18 having been digested with SmaI. A plasmid thus obtained was designated as pUC18DDH.

Figure 10:
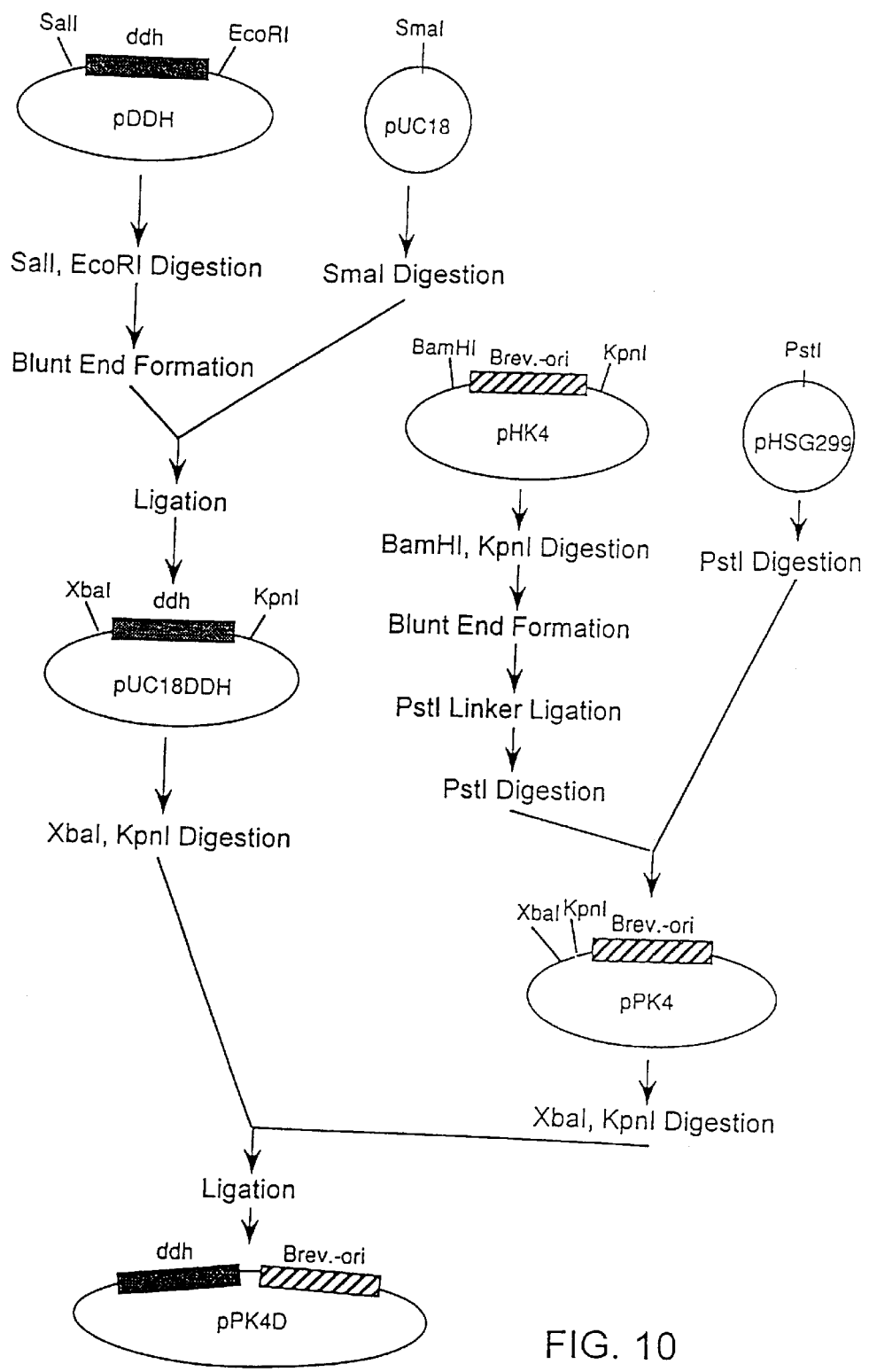
FIG. 10 illustrates a process of construction of a plasmid pPK4D comprising ddh and Brevi.-ori.

Brevi.-ori was introduced into pUC18DDH to construct a plasmid carrying ddh autonomously replicable in coryneform bacteria. pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated PstI linker (produced by Takara Shuzo) was ligated so that it was inserted into a PstI site of pHSG299. A plasmid constructed as described above was designated as pPK4. Next, pUC18DDH was digested with XbaI and KpnI, and a generated fragment was ligated with pPK4 having been digested with KpnI and XbaI. Thus a plasmid containing ddh autonomously replicable in coryneform bacteria was constructed. This plasmid was designated as pPK4D. The process of construction of pPK4D is shown in FIG. 10.

Comparative Example 2

Figure 11:
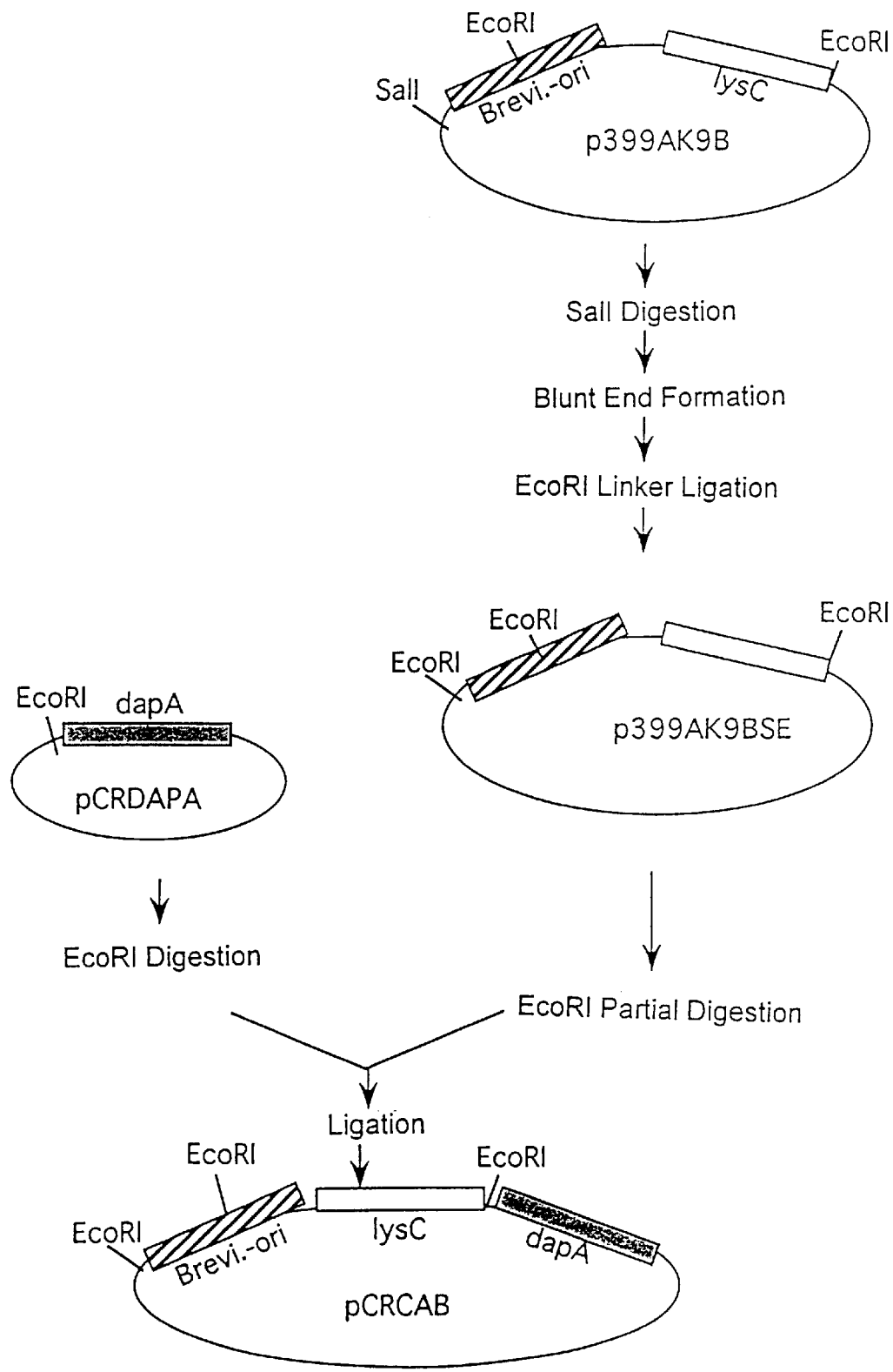
FIG. 11 illustrates a process of construction of a plasmid PCRCAB comprising lysC, dapA and Brevi.-ori.

Construction of Plasmid Comprising Combination of Mutant lysC, and dapA, dapB or ddh <1> Construction of Combination of Mutant lysC and dapA A plasmid comprising mutant lysC, dapA, and replication origin of coryneform bacteria was constructed from the plasmid pCRDAPA comprising dapA and the plasmid p399AK9B comprising mutant lysC and Brevi.-ori. p399AK9B was completely digested with SalI, and then it was blunt-ended. An EcoRI linker was ligated thereto to construct a plasmid in which the SalI site was modified into an EcoRI site. The obtained plasmid was designated as p399AK9BSE. The mutant lysC and Brevi.-ori were excised as one fragment by partially digesting p399AK9BSE with EcoRI. This fragment was ligated with pCRDAPA having been digested with EcoRI. An obtained plasmid was designated as pCRCAB. This plasmid is autonomously replicable in *E. coli* and coryneform bacteria, and it gives kanamycin resistance to a host, the plasmid comprising a combination of mutant lysC and dapA. The process of construction of pCRCAB is shown in FIG. 11.

<2> Construction of Plasmid Comprising Combination of Mutant lysC and dapB

A plasmid comprising mutant lysC and dapB was constructed from the plasmid p399AK9 having mutant lysC and the plasmid p399DPR having dapB. A fragment of 1,101 bp containing a structural gene of DDPR was extracted by digesting p399DPR with EcoRV and SphI. This fragment was ligated with p399AK9 having been digested with SalI and then blunt-ended and having been further digested with SphI to construct a plasmid comprising a combination of mutant lysC and dapB. This plasmid was designated as p399AKDDPR.

Figure 12:
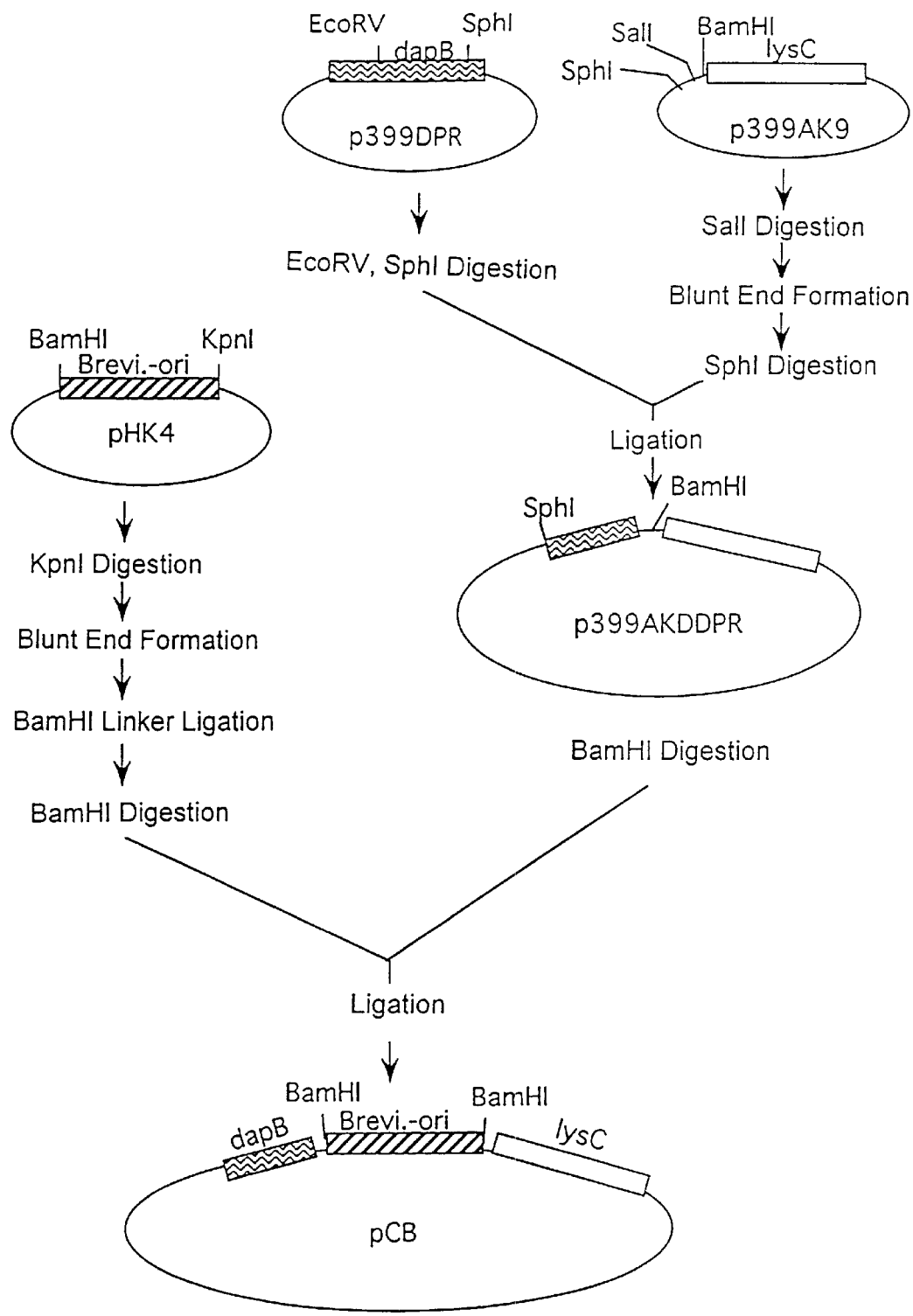
FIG. 12 illustrates a process of construction of a plasmid pCB comprising mutant lysC, dapB, and Brevi.-ori.

Next, Brevi.-ori was introduced into the obtained p399AKDDPR. The plasmid pHK4 containing Brevi.-ori was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKDDPR having been also digested with BamHI to construct a plasmid containing mutant lysC and dapB autonomously replicable in coryneform bacteria. The constructed plasmid was designated as pCB. The process of construction of pCB is shown in FIG. 12.

<3> Construction of Plasmid Comprising Combination of mutant lysC and ddh

A plasmid containing mutant lysC, ddh, and a replication origin for coryneform bacteria was prepared from plasmid pUC18DDH containing ddh and plasmid p399AK9B containing mutant lysC and Brevi.-ori. pUC18DDH was digested with a restriction enzyme EcoRI (produced by Takara Shuzo), blunt-ended and ligated with a SalI polylinker at a terminal thereof to change EcoRI site to SalI site. The obtained plasmid was digested with SaLI to obtain a DNA fragment containing ddh.

Figure 13:
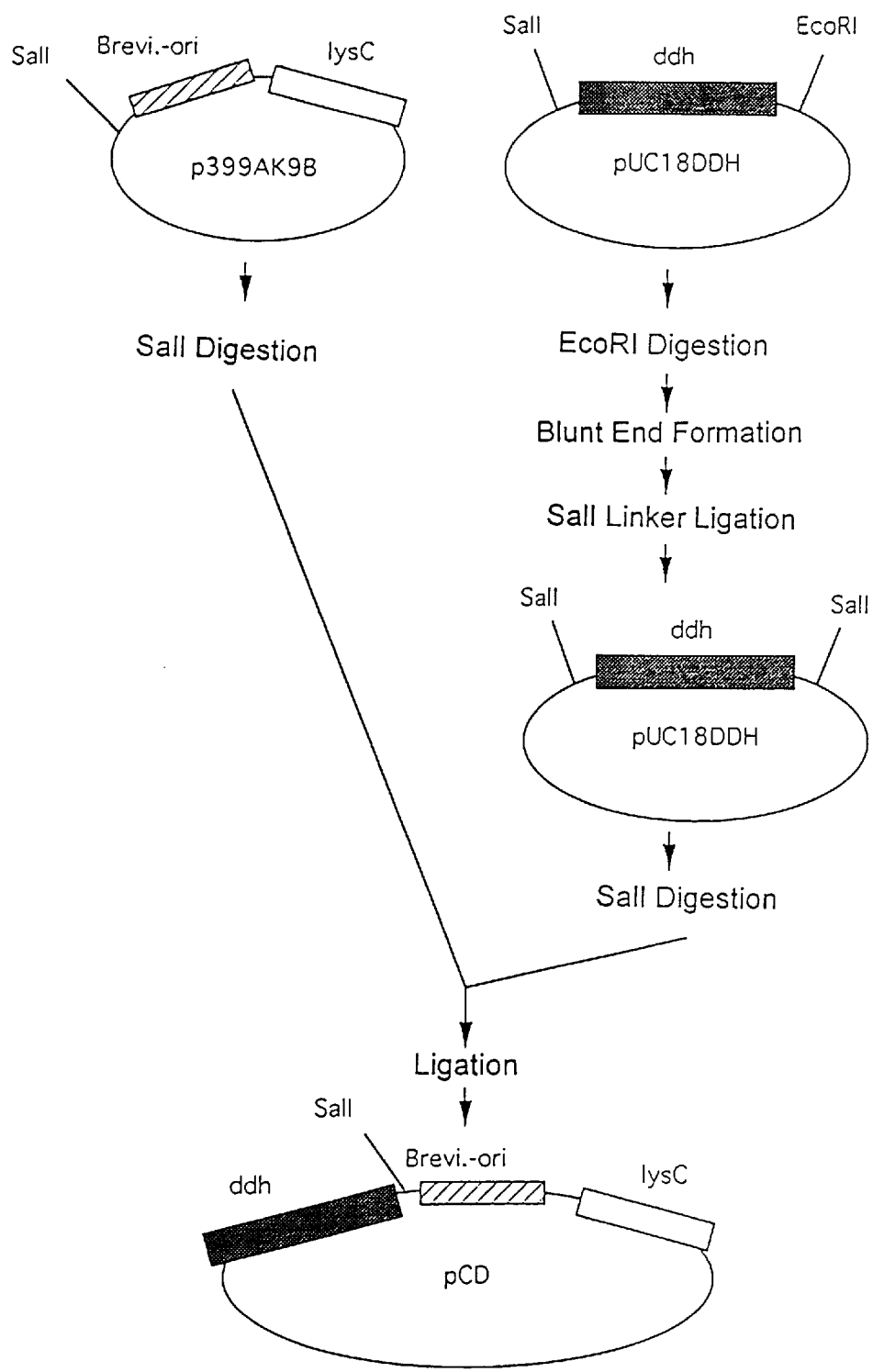
FIG. 13 illustrates a process of construction of a plasmid pCD comprising mutant lysC and ddh.

Then, p399AK9B was digested with a restriction enzyme SalI and ligated with the DNA fragment containing ddh. Thus, a plasmid containing mutant lysC, ddh and Brevi.-ori autonomously replicable in coryneform bacteria was prepared, and designated as pCD. The process of construction of pCD is shown in FIG. 13.

Example 5

Introduction of Plasmids Comprising Genes for L-Lysine Biosynthesis into L-Lysine-Producing Bacterium of *Brevibacterium lactofermentum*

The plasmids comprising the genes for L-lysine biosynthesis constructed as described above, namely p399AK9B (Cm$^r$), pLYSAB(Cm$^r$), pPwm(Km$^r$), pCRCAB(Km$^r$), pCB (Cm$^r$), pCD(Cm$^r$), and pCL(Cm$^r$) were introduced into an L-lysine-producing bacterium AJ11082 (NRRL B-11470) of *Brevibacterium lactofermentum* respectively. AJ11082 strain has a property of AEC resistance. The plasmids were introduced in accordance with an electric pulse method (Sugimoto et al., Japanese Patent Application Laid-open No. 2-207791). Transformants were selected based on drug resistance markers possessed by the respective plasmids. Transformants were selected on a complete medium containing 5 µg/ml of chloramphenicol when a plasmid comprising a chloramphenicol resistance gene was introduced, or transformants were selected on a complete medium containing 25 µg/ml of kanimaycin when a plasmid comprising a kanamycin resistance gene was introduced.

To a strain which mutant lysC and lysA were enhanced among the obtained transformants, pPwm (Km$^r$) was introduced to obtain a strain in which three of mutant lysC, lysA and ppc were enhanced (AJ11082/pCL/pPwm). Transformants were selected on a complete medium containing 5 µg/ml of chloramphenicol and 25 µg/ml of kanamycin.

Example 6

Production of L-Lysine

Each of the transformants obtained in Example 5 was cultivated in an L-lysine-producing medium to evaluate its L-lysine productivity. The L-lysine-producing medium had the following composition.

[L-Lysine-producing Medium]

The following components other than calcium carbonate (in 1 L) were dissolved, and pH was adjusted at 8.0 with KOH. The medium was sterilized at 115° C. at for 15 minutes, and calcium carbonate (50 g) having been separately sterilized in hot air in a dry state was thereafter added thereto.

| | |
|---|---:|
| Glucose | 100 g |
| (NH$_4$)$_2$SO$_4$ | 55 g |
| KH$_2$PO$_4$ | 1 g |
| MgSO$_4$·7H$_2$O | 1 g |
| Biotin | 500 µg |
| Thiamin | 2000 µg |
| FeSO$_4$·7H$_2$O | 0.01 g |
| MnSO$_4$·7H$_2$O | 0.01 g |
| Nicotinamide | 5 mg |
| Protein hydrolysate (Mamenou) | 30 ml |
| Calcium carbonate | 50 g |

Each of the various types of the transformants and the parent strain was inoculated to the medium having the composition described above to perform cultivation at 31.5° C. with reciprocating shaking. The amount of produced L-lysine after 40 or 72 hours of cultivation are shown in Table 1. In the table, lysC* represents mutant lysc.

TABLE 1

Accumulation of L-Lysine after Cultivation for 40 or 72 Hours

| Bacterial strain/plasmid | Introduced gene | Amount of produced L-lysine(g/L) after 40 hrs | after 72 hrs |
|---|---|---|---|
| AJ11082 | | 22.0 | 29.8 |
| AJ11082/p399AK9B | lysC* | 16.8 | 34.5 |
| AJ11082/pLYSAB | lysA | 19.8 | 32.5 |
| AJ11082/pPwm | ppc | 20.7 | 28.9 |
| AJ11082/pCRCAB | lysC*, dapA | 19.7 | 36.5 |
| AJ11082/pCB | lysC*, dapB | 23.3 | 35.0 |
| AJ11082/pCD | lysC*, ddh | 15.0 | 27.0 |
| AJ11082/pCL | lysC*, lysA | 24.0 | 44.0 |
| AJ11082/pCL/pPwm | lysC*, lysA, ppc | 25.0 | 45.2 |

As shown in above, when mutant lysC, lysA, or ppc was enhanced singly, or when mutant lysC was enhanced in combination with dapA or ddh, the amount of produced L-lysine was larger than or equivalent to that produced by the parent strain after 72 hours of cultivation, however, the amount of produced L-lysine was smaller than that produced by the parent strain after 40 hours of cultivation. Namely, the L-lysine-producing speed was lowered in cultivation for a short period. Similarly, when mutant lysC and ddh were enhanced in combination, the amount of produced L-lysine was smaller than that produced by the parent strain after 40 hours and 72 hours of cultivation. On the contrary, in the case of the strain in which dapB was enhanced together with mutant lysC, the growth was improved, the L-lysine-producing speed was successfully restored in the short period of cultivation, and the accumulated amount of L-lysine was also improved in the long period of cultivation. In the case of the strain in which three of mutant lysC, lysA, and ppc were simultaneously enhanced, the L-lysine productivity was further improved.

What is claimed is:

1. A recombinant DNA autonomously replicable in cells of coryneform bacteria, comprising:
   a DNA sequence encoding an aspartokinase which is substantially insensitive to feedback inhibition by L-lysine and L-threonine, and
   a DNA sequence encoding a diaminopimelate decarboxylase, wherein
   the DNA sequence encoding the aspartokinase is a DNA encoding a wild-type aspartokinase which is substantially insensitive to feedback inhibition by L-lysine and L-threonine or a DNA encoding an aspartokinase which is substantially insensitive to feedback inhibition by L-lysine and L-threonine and which has been produced by treating a DNA encoding a wild-type aspartokinase with a mutagen; and
   the DNA sequence encoding the diaminopimelate decarboxylase is a DNA encoding a wild-type diaminopimelate decarboxylase or a DNA encoding a diaminopimelate decarboxylase which has been treated with a mutagen and retains diaminopimelate decarboxylase activity.

2. The recombinant DNA of claim 1, wherein the encoded aspartokinase is a mutant of an aspartokinase originating from coryneform bacteria in which the amino acid residue corresponding to the alanine residue at the 279th position as counted from the N-terminus in the amino acid sequence of SEQ ID NO: 5 is an amino acid residue other than an alanine residue or an acidic amino acid residue, and the amino acid residue corresponding to the alanine residue at the 30th position as counted from the N-terminus in the amino acid sequence of SEQ ID NO: 7 is an amino acid residue other than an alanine residue or an acidic amino acid residue.

3. The recombinant DNA of claim 1, wherein the encoded diaminopimelate decarboxylase has the amino acid sequence of SEQ ID NO: 12.

4. The recombinant DNA of claim 1, wherein the DNA sequence encoding the aspartokinase hybridizes to SEQ ID NO: 3 under stringent conditions.

5. The recombinant DNA of claim 4, wherein said stringent conditions comprise 1×SSC.

6. The recombinant DNA of claim 4, wherein said stringent condition comprises 0.1×SSC.

7. The recombinant DNA of claim 1, wherein the DNA sequence encoding a diaminopimelate decarboxylase comprises SEQ ID NO: 11.

8. The recombinant DNA of claim 1, further comprising a DNA sequence coding for a phosphoenolpyruvate carboxylase, wherein the DNA sequence coding for a phosphoenolpyruvate carboxylase encodes a wild-type phosphoenolpyruvate carboxylase or is produced by treating a DNA encoding a phosphoenolpyruvate carboxylase with a mutagen and retains phosphoenolpyruvate carboxylase activity.

9. A coryneform bacterium transformed with the recombinant DNA of claim 1.

10. A coryneform bacterium transformed with the recombinant DNA of claim 8.

11. A method for producing L-lysine comprising:
    cultivating the coryneform bacterium of claim 9 in an appropriate culture medium to allow L-lysine to be produced and accumulated in the culture, and collecting the L-lysine from the culture.

12. A method for producing L-lysine comprising:
    cultivating the coryneform bacterium of claim 10 in an appropriate culture medium to allow L-lysine to be produced and accumulated in the culture, and collecting the L-lysine from the culture.

13. A method for producing L-lysine comprising:
    cultivating a coryneform bacterium transformed with a recombinant DNA in an appropriate culture medium to allow L-lysine to be produced and accumulated in the culture, and collecting the L-lysine from the culture,
    wherein the recombinant DNA comprises:
        a DNA sequence encoding an aspartokinase in which feedback inhibition by L-lysine and L-threonine is desensitized, and a DNA sequence encoding a diaminopimelate decarboxylase.

14. The method of claim 13, wherein the DNA sequence encoding the aspartokinase is a DNA encoding a wild-type aspartokinase which is substantially insensitive to feedback inhibition by L-lysine and L-threonine or a DNA encoding an aspartokinase which is substantially insensitive to feedback inhibition by L-lysine and L-threonine and which has been produced by treating a DNA encoding a wild-type aspartokinase with a mutagen; and the DNA sequence encoding the diaminopimelate decarboxylase is a DNA encoding a wild-type diaminopimelate decarboxylase or a DNA encoding a diaminopimelate decarboxylase which has been treated with a mutagen and retains diaminopimelate decarboxylase activity.

15. The method claim 13, wherein the encoded aspartokinase is a mutant of an aspartokinase originating from coryneform bacteria in which the amino acid residue corresponding to the alanine residue at the 279th position as counted from the N-terminus in the amino acid sequence of SEQ ID NO: 5 is a threonine residue, and the amino acid residue corresponding to the alanine residue at the 30th position as counted from the N-terminus in the amino acid sequence of SEQ ID NO: 7 is threonine residue.

16. The method of claim 13, wherein the encoded diaminopimelate decarboxylase has the amino acid sequence of SEQ ID NO: 12.

17. The method of claim 13, wherein the DNA sequence encoding the aspartokinase hybridizes to SEQ ID NO: 3 under stringent conditions.

18. The method of claim 17, wherein said stringent conditions comprise 1×SSC.

19. The method of claim 18, wherein said stringent condition comprises 0.1×SSC.

20. The method of claim 13, wherein encoded aspartokinase has an α-subunit having the amino acid sequence of SEQ ID NO: 5 in which the alanine residue at the 279th position as counted from the N-terminus of SEQ ID NO: 5 is an amino acid residue other than an alanine residue or an acidic amino acid residue, and has an β-subunit having the amino acid sequence of SEQ ID NO: 7 in which the alanine residue at the 30th position as counted from the N-terminus of SEQ ID NO: 7 is an amino acid residue other than an alanine residue or an acidic amino acid residue.

21. The method of claim 13, wherein the DNA sequence encoding a diaminopimelate decarboxylase comprises SEQ ID NO: 11.

22. The method of claim 13, further comprising a DNA sequence coding for a phosphoenolpyruvate carboxylase, wherein the DNA sequence coding for a phosphoenolpyruvate carboxylase encodes a wild-type phosphoenolpyruvate carboxylase or is produced by treating a DNA encoding a phosphoenolpyruvate carboxylase with a mutagen and retains phosphoenolpyruvate carboxylase activity.

* * * * *